United States Patent
Hanson et al.

(10) Patent No.: US 10,584,077 B2
(45) Date of Patent: Mar. 10, 2020

(54) ATROPISOMERS AND METHODS OF ALTERING ENANTIOMERIC EXCESS

(71) Applicant: Florida State University Research Foundation, Inc., Tallahassee, FL (US)

(72) Inventors: Kenneth Hanson, Tallahassee, FL (US); Suliman A. Ayad, Tallahassee, FL (US); Victoria A. Posey, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/854,885

(22) Filed: Dec. 27, 2017

(65) Prior Publication Data

US 2018/0179120 A1     Jun. 28, 2018

Related U.S. Application Data

(60) Provisional application No. 62/439,317, filed on Dec. 27, 2016.

(51) Int. Cl.

| | |
|---|---|
| *C07B 55/00* | (2006.01) |
| *C07C 309/71* | (2006.01) |
| *C07C 68/06* | (2006.01) |
| *C07C 69/96* | (2006.01) |
| *C07C 227/36* | (2006.01) |
| *C07D 209/18* | (2006.01) |
| *C07D 207/16* | (2006.01) |
| *C07C 229/06* | (2006.01) |

(52) U.S. Cl.
CPC ............ *C07B 55/00* (2013.01); *C07C 68/06* (2013.01); *C07C 69/96* (2013.01); *C07C 227/36* (2013.01); *C07C 229/06* (2013.01); *C07C 309/71* (2013.01); *C07D 207/16* (2013.01); *C07D 209/18* (2013.01); *C07B 2200/07* (2013.01); *C07C 2601/14* (2017.05); *C07C 2602/42* (2017.05)

(58) Field of Classification Search
None
See application file for complete search history.

(56) References Cited

PUBLICATIONS

Panchal, Bhavesh M. Convenient and highly efficient chromatographic resolution of BINOL and of 6,6'-dibromo-BINOL via N(α)-Boc-tryptophan esters. Tetrahedron Letters. 43 (2002) 9245-9248.*
Li, Yannian. Azoarenes with Opposite Chiral Configurations: Light-Driven Reversible Handedness Inversion in Self-Organized Helical Superstructures. Angew. Chem. Int. Ed. 2013, 52, 8925-8929.*
Alkorta et al., "Static and Dynamic Properties of 1,1'-Bi-2-naphthol and Its Conjugated Acids and Bases," Chem. Eur. J., 2014, 20:14816-14825.
Chow et al., "A Versatile Method for the Resolution and Absolute Configuration Assignment of Substituted 1,1'-Bi-2-naphthols," J. Org. Chem., 1996, 61:8712-8714.
Panchal et al., "Convenient and Highly Efficient Chromatographic Resolution of Binol and of 6,6'-dibromo-BINOL via N(α)-Boc-tryptophan Esters," Tetrahedron Letters, 2002, 43:9245-9248.
Lv et al., "Thermodynamic Studies of (R)-Binol-Menthyl Dibarbonates, Journal of Thermal Analysis and Calorimetry," 2006, 86(2)541-546.

* cited by examiner

*Primary Examiner* — Samantha L Shterengarts
(74) *Attorney, Agent, or Firm* — Eversheds Sutherland (US) LLP

(57) ABSTRACT

Provided herein are methods of altering enantiomeric excess. The methods may include irradiating an atropisomer that includes at least one chiral substituent to alter the enantiomeric excess of the atropisomer. The at least one chiral substituent may be removed following irradiation.

19 Claims, 8 Drawing Sheets

Formula (AA)

Formula (BB)

Formula (AA')

Formula (BB')

ATROPISOMERS AND METHODS OF ALTERING ENANTIOMERIC EXCESS

CROSS-REFERENCE TO RELATED APPLICATIONS

This application claims priority to U.S. Provisional Patent Application No. 62/439,317, filed Dec. 27, 2016, which is incorporated herein by reference.

BACKGROUND

Enantioselective synthesis may be considered an important part of modern synthetic chemistry, and can be used in the production of certain chemicals, such as food additives, fragrances, natural products, and pharmaceuticals.

A frequently-used compound for enantioselective reactions is 1,1'-bi-2-naphthol ("BINOL"). The most common methods to synthesize BINOL and its derivatives, however, result in the formation of a racemic mixture of (R) and (S) isomers. Due to the fact that only a single isomer of BINOL is required for most, if not all, enantioselective reactions, the racemic mixture typically is purified through chromatography or recrystallization to achieve the desired isomer, while the other isomer typically is discarded.

There remains a need for methods of altering the enantiomeric excess of compounds, such as BINOL, BINOL derivatives, and other atropisomers, including racemic mixtures thereof.

BRIEF SUMMARY

Provided herein are methods of altering the enantiomeric excess of atropisomers by subjecting the atropisomers to radiation, such as electromagnetic radiation.

In some embodiments, the methods include providing an atropisomer having an enantiomeric excess of 0% to 100%, wherein the atropisomer includes at least one chiral substituent; and irradiating the atropisomer to alter the enantiomeric excess. In some embodiments, the enantiomeric excess is 0% to about 5% prior to the irradiating of the atropisomer, and the atropisomer is a racemic atropisomer. In some embodiments, the providing of the atropisomer includes contacting an unsubstituted atropisomer with a chiral substituent precursor to form the atropisomer. The unsubstituted atropisomer may include a hydroxyl functional group, and the chiral substituent precursor may include an ester functional group or an acyl halide functional group.

Also provided herein are atropisomers. In some embodiments, the atropisomers have a structure according to formula (I), (II), (III), or (IV):

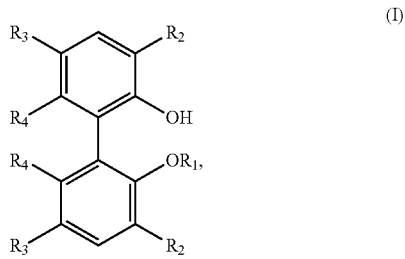

(I)

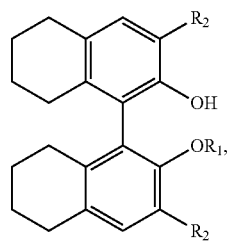

(II)

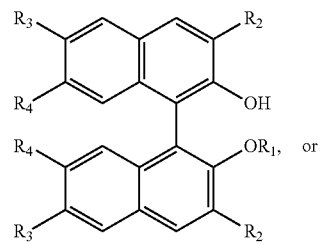

(III)

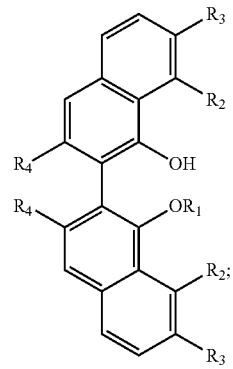

(IV)

wherein (i) $R_1$ is a $C_1$-$C_{30}$ hydrocarbyl comprising at least one chiral atom, (ii) $R_2$ is independently selected from hydrogen, a $C_1$-$C_{30}$ hydrocarbyl, or a halogen, (iii) $R_3$ is independently selected from hydrogen, a $C_1$-$C_{30}$ hydrocarbyl, or a halogen, and (iv) $R_4$ is independently selected from hydrogen or a halogen.

DETAILED DESCRIPTION

Provided herein are methods of altering enantiomeric excess. Also provided herein are compounds, including atropisomers. In some embodiments, the compounds may be irradiated to alter the enantiomeric excess. For example, an atropisomer may be provided as a racemic mixture, and an enantiomeric excess of one isomer may be obtained by irradiating the atropisomer. The extent to which the enantiomeric excess is altered may be controlled by the methods provided herein.

Methods

In some embodiments, the methods of altering enantiomeric excess include providing an atropisomer having an enantiomeric excess of 0% to 100%, wherein the atropisomer comprises at least one chiral substituent; and irradiating the atropisomer to alter the enantiomeric excess.

The "atropisomers" of the methods provided herein generally may include any compound that allows for the isolation of conformers resulting from hindered rotation about a single bond.

The "at least one chiral substituent" generally may include any moiety that (i) includes at least one chiral atom, (ii) can be covalently bonded to an atropisomer, and (iii) permits an enantiomeric excess to be altered according to the methods provided herein. In some embodiments, the at least one chiral substituent includes a $C_1$-$C_{30}$ hydrocarbyl, the $C_1$-$C_{30}$ hydrocarbyl including at least one chiral atom.

Not wishing to be bound by any particular theory, it is believed that the at least one chiral substituent may determine, at least in part, (i) the extent of the enantiomeric excess achieved by the methods provided herein, (ii) the isomer (i.e., the (R) or (S) enantiomer) that is provided in excess by the methods provided herein, or (iii) a combination thereof.

In some embodiments, the atropisomer having an enantiomeric excess of 0% to 100% includes a compound of formula (I), (II), (III), or (IV):

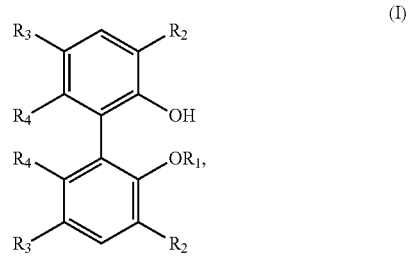
(I)

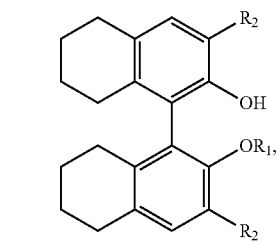
(II)

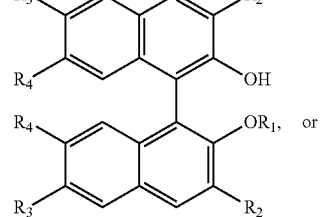
(III)

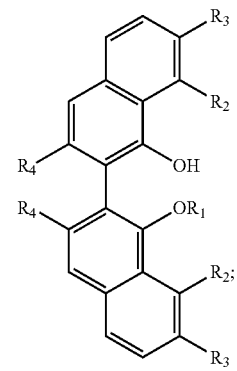
(IV)

wherein (i) $R_1$ is the at least one chiral substituent, (ii) $R_2$ is independently selected from hydrogen, a $C_1$-$C_{30}$ hydrocarbyl, or a halogen, (iii) $R_3$ is independently selected from hydrogen, a $C_1$-$C_{30}$ hydrocarbyl, or a halogen, and (iv) $R_4$ is independently selected from hydrogen or a halogen.

In some embodiments, $R_1$ is a $C_1$-$C_{30}$ hydrocarbyl that includes at least one chiral atom. For example, $R_1$ may be a substituent selected from formula (A) or (B):

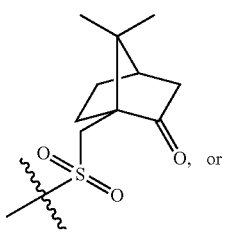
(A)

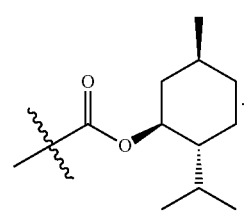
(B)

Figure 4A:
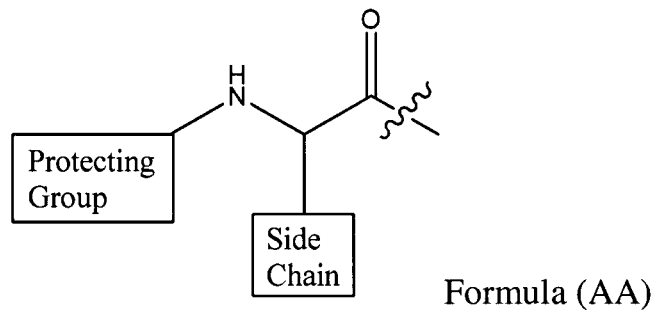
FIG. 4A depicts an embodiment of an N-protected amino acid substituent.
Figure 4B:
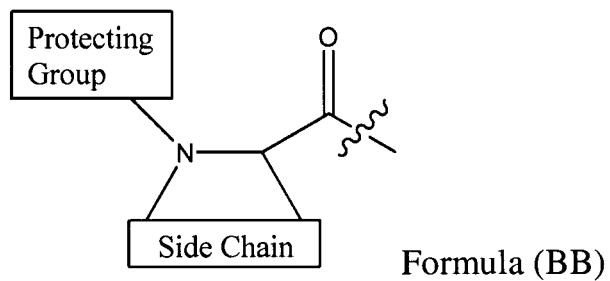
FIG. 4B depicts an embodiment of an N-protected amino acid substituent.

As a further example, R₁ may be an N-protected amino acid substituent. The "N-protected amino acid substituent" generally may include any known amino acid substituent that includes a protecting group covalently bonded to the amine functional group. For example, the N-protected amino acid substituent may have a structure according to Formula (AA), as depicted at FIG. 4A, or Formula (BB), as depicted at FIG. 4B.

The side chain of Formula AA or BB may include the side chain of any known amino acid, including the 20 amino acids of the genetic code. In some embodiments, the side chain of Formula AA is that of phenylalanine (Phe), phenylglycine (Phg), or tryptophan (Trp), and the side chain of Formula BB is that of proline (Pro).

The protecting group of Formula AA or BB generally may include any known amine protecting group. Non-limiting examples of protecting groups include the following: carbobenzyloxy (Cbz), tert-Butyloxycarbonyl (Boc), p-methoxybenzyl carbonyl (Moz), 9-fluorenylmethyloxycarbonyl (FMOC), acetyl (Ac), benzoyl (Bz), benzyl (Bn), carbamates, p-methoxybenzyl (Pmb), 3,4-dimethoxybenzyl (Dmpm), p-methoxyphenyl (Pmp), tosyl (Ts), and trichloroethyl chloroformate (Troc).

In some embodiments, the N-protected amino acid substituent has a structure according to formula (1), (2), (3), (4), (5), or (6):

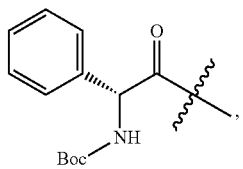
(1)

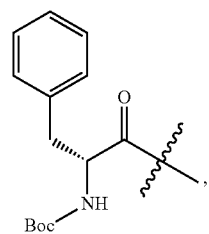
(2)

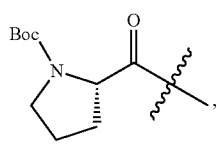
(3)

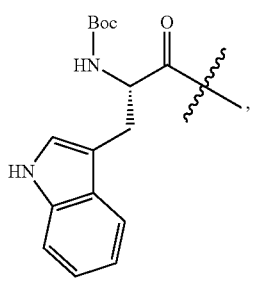
(4)

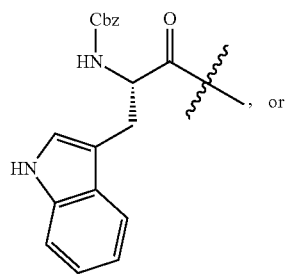
(5)
, or

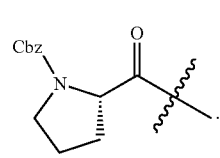
(6)

In some embodiments, the atropisomer having an enantiomeric excess of 0% to 100% includes a compound of formula (I), (II), (III), or (IV), wherein R₂ is independently selected from the following substituents:

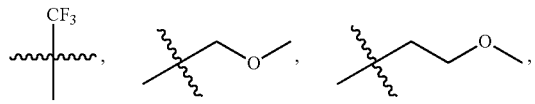

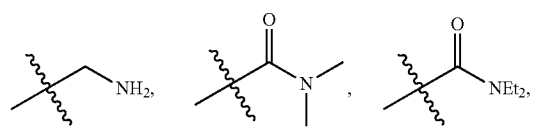

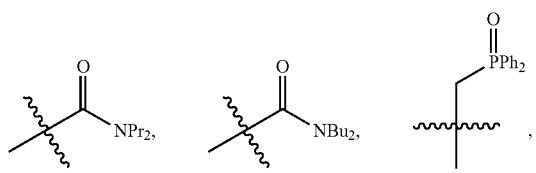

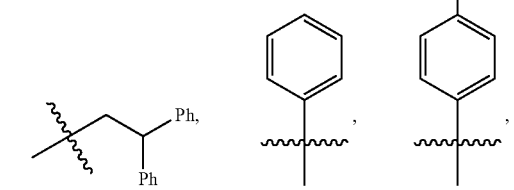

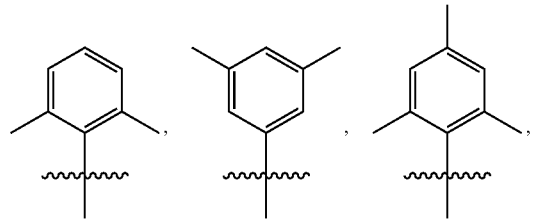

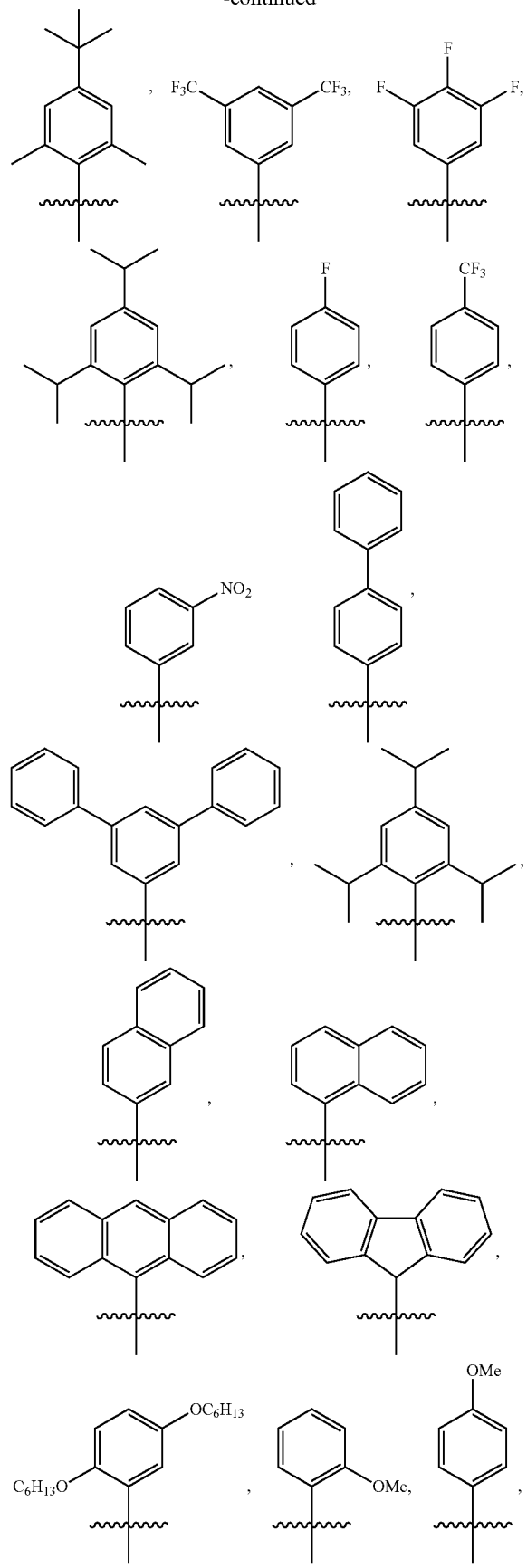
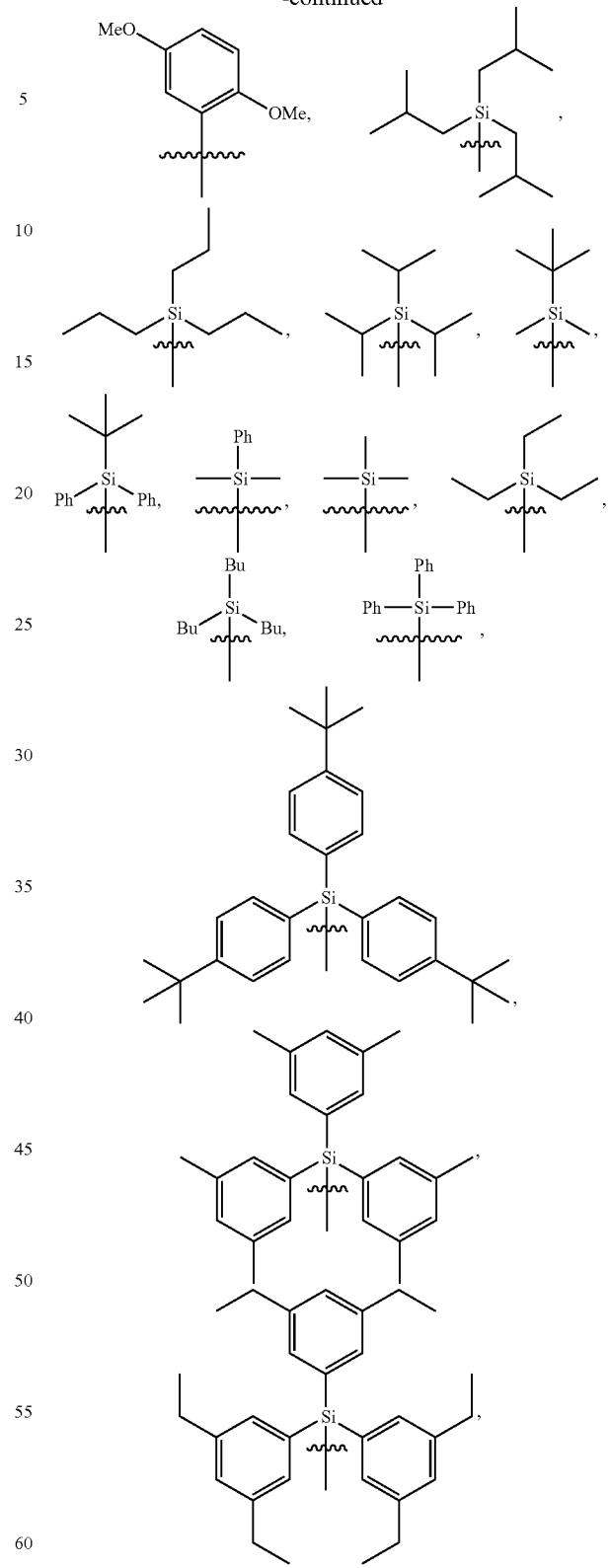
4-β-naphthylphenyl, 4-t-BuC$_6$H$_4$, or 3,5-t-Bu$_2$C$_6$H$_3$.
In some embodiments, the atropisomer having an enantiomeric excess of 0% to 100% includes a compound of formula (I), (II), (III), or (IV), wherein R$_3$ is independently selected from the following substituents:

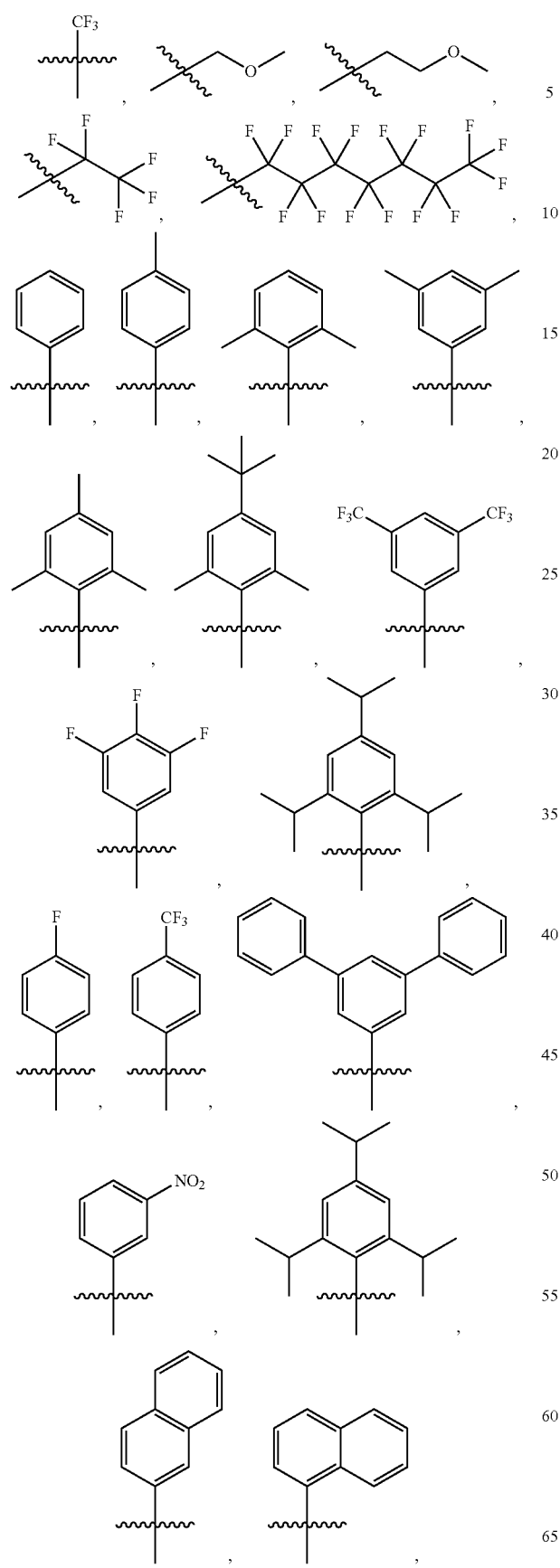
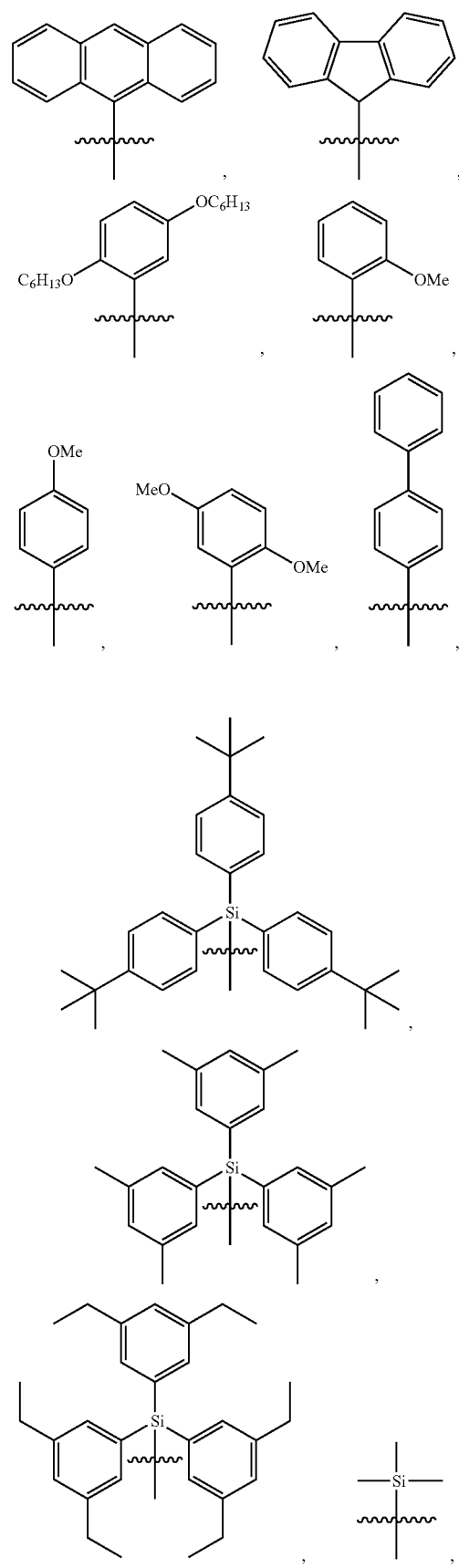

-continued

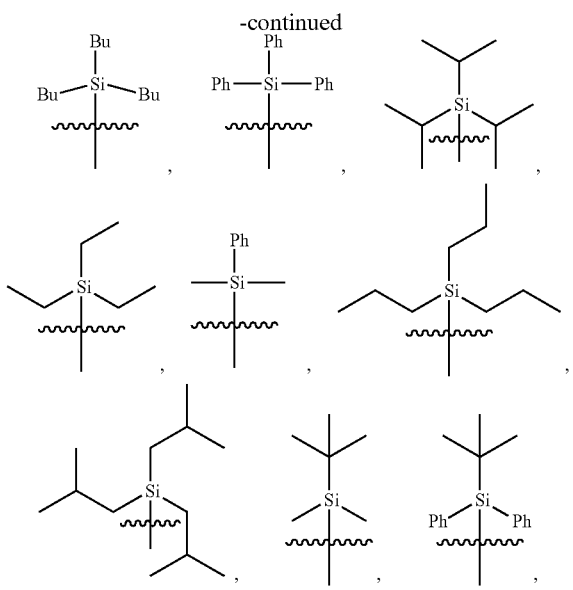

4-β-naphthylphenyl, 4-t-BuC$_6$H$_4$, or 3,5-t-Bu$_2$C$_6$H$_3$.

In some embodiments, the atropisomer having an enantiomeric excess of 0% to 100% includes a compound of formula (V):

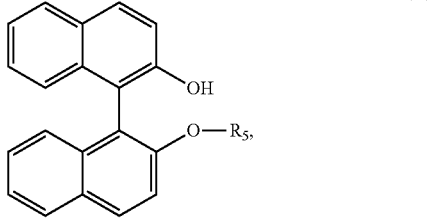

wherein R$_5$ is a substituent that (i) includes at least one chiral atom, and (ii) has a molecular weight of about 40 g/mol to about 400 g/mol. In some embodiments, R$_5$ is selected from Boc-Phg (Formula (1)), Boc-Phe (Formula (2)), Boc-Pro (Formula (3)), Boc-Trp (Formula (4)), Cbz-Trp (Formula (5)), Cbz-Pro (Formula (6)), Men-Form (Formula (B)), or Camph-Sulf (Formula (A)).

In some embodiments, the atropisomer is a racemic atropisomer prior to the irradiating of the atropisomer. As used herein, the phrase "racemic atropisomer" generally includes atropisomers having an enantiomeric excess of 0% to about 5% prior to the irradiating of the atropisomer.

In some embodiments, the atropisomer is an enantiopure atropisomer. As used herein, the phrase "enantiopure atropisomer" generally includes atropisomers having an enantiomeric excess of about 95% to 100% prior to the irradiating of the atropisomer.

Generally, an isomer that may be present in any excess in the atropisomers—prior to or after irradiation—may be the (R) or (S) isomer. Therefore, the enantiomeric excess (ee) may, in some embodiments, be the absolute value of [((R−S)/(R+S))*100], wherein "R" and "S" are the mols of the (R) and (S) isomers, respectively, that are present in a sample. For example, an atropisomer, prior to irradiation, may be a racemic atropisomer that includes 50% of the (R) isomer and 50% of the (S) isomer, and, after radiation, the atropisomer may include 80% of the (R) isomer and 20% of the (S) isomer, i.e., an enantiomeric excess of 60%. As a further example, an atropisomer, prior to irradiation, may be a racemic atropisomer that includes 50% of the (R) isomer and 50% of the (S) isomer, and, after radiation, the atropisomer may include 70% of the (S) isomer and 30% of the (R) isomer, i.e., an enantiomeric excess of 40%. As yet another example, an atropisomer, prior to irradiation, may include 60% of the (R) isomer and 40% of the (S) isomer, i.e., an enantiomeric excess of 20%, and, after radiation, the atropisomer may include 20% of the (R) isomer and 80% of the (R) isomer, i.e., an enantiomeric excess of 60%.

Generally, the irradiating of the atropisomers may alter the enantiomeric excess of the atropisomers by any amount. In some embodiments, the irradiating of the atropisomers alters the enantiomeric excess by about 3 percentage points to 100 percentage points. For example, an enantiomeric excess of 40% that is altered by 3 percentage points will result in an enantiomeric excess of 37% or 43%. In some embodiments, the irradiating of the atropisomers alters the enantiomeric excess by about 3 percentages points to about 80 percentage points. In some embodiments, the irradiating of the atropisomers alters the enantiomeric excess by about 3 percentages points to about 70 percentage points. In some embodiments, the irradiating of the atropisomers alters the enantiomeric excess by about 5 percentages points to about 70 percentage points. In some embodiments, the irradiating of the atropisomers alters the enantiomeric excess by about 10 percentages points to about 70 percentage points. In some embodiments, the irradiating of the atropisomers alters the enantiomeric excess by about 20 percentages points to about 70 percentage points. In some embodiments, the irradiating of the atropisomers alters the enantiomeric excess by about 25 percentages points to about 70 percentage points. In some embodiments, the irradiating of the atropisomers alters the enantiomeric excess by about 30 percentages points to about 70 percentage points. In some embodiments, the irradiating of the atropisomers alters the enantiomeric excess by about 40 percentages points to about 70 percentage points. In some embodiments, the irradiating of the atropisomers alters the enantiomeric excess by about 50 percentages points to about 70 percentage points.

Not wishing to be bound by any particular theory, a substituent comprising at least one chiral atom may be selected to increase the enantiomeric excess of one isomer versus another. For example, in some embodiments, the atropisomer that is irradiated includes a compound of formula (V):

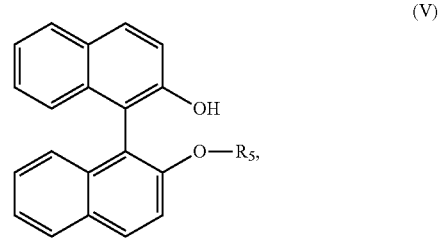

wherein R$_5$ is selected from Boc-Phg (Formula (1)), Boc-Phe (Formula (2)), Boc-Pro (Formula (3)), Boc-Trp (Formula (4)), Cbz-Trp (Formula (5)), Cbz-Pro (Formula (6)), Men-Form (Formula (B)), or Camph-Sulf (Formula (A)); and wherein the irradiation of the atropisomer (i) increases the enantiomeric excess of the (S) isomer (and decreases the enantiomeric excess of the (R) isomer) when $R_5$ is selected from Boc-Phg, Boc-Pro, Boc,-Trp, Cbz-Trp, Cbz-Pro, or Camph-Sulf, and (ii) increases the enantiomeric excess of the (R) isomer (and decreases the enantiomeric excess of the (S) isomer) when $R_5$ is Men-Form. One or more other conditions also may be used to selectively increase the enantiomeric excess of one isomer, and the foregoing chiral substituents may selectively increase the enantiomeric excess of different isomers depending on the structure of the atropisomer, the intensity and/or duration of the irradiation, etc.

In some embodiments, the providing of the atropisomer includes contacting an unsubstituted atropisomer with a chiral substituent precursor to form the atropisomer, wherein the unsubstituted atropisomer includes a first functional group, and the chiral substituent precursor includes a second functional group that is capable of forming a covalent bond upon contacting the first functional group. In some embodiments, the unsubstituted atropisomer includes a hydroxyl functional group, and the chiral substituent precursor includes an ester functional group or an acyl halide functional group.

The chiral substituent precursor generally may be any compound capable of [1] covalently bonding with an atropisomer, and [2] forming one of the chiral substituents described herein.

Figure 5A:
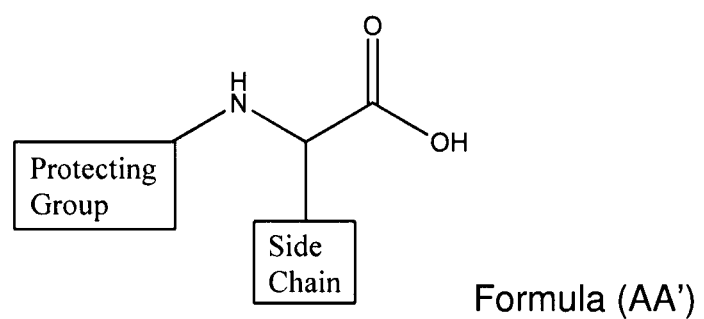
FIG. 5A depicts an embodiment of an N-protected amino acid.
Figure 5B:
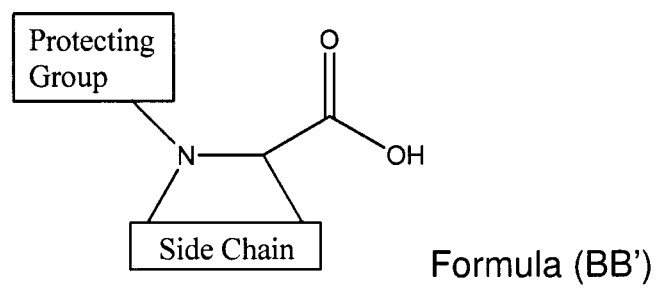
FIG. 5B depicts an embodiment of an N-protected amino acid.

In some embodiments, the chiral substituent precursor includes an N-protected amino acid. The "N-protected amino acid" generally may include any known amino acid that includes a protecting group covalently bonded to the amine functional group. For example, the N-protected amino acid may have a structure according to the following Formula (AA'), as depicted at FIG. 5A, or Formula (BB'), as depicted at FIG. 5B.

The side chain of Formula AA' or BB' may include the side chain of any known amino acid, including the 20 amino acids of the genetic code. In some embodiments, the side chain of Formula AA' is that of phenylalanine (Phe), phenylglycine (Phg), or tryptophan (Trp), and the side chain of Formula BB' is that of proline (Pro).

The protecting group of Formula AA' or BB' generally may include any known amine protecting group. Non-limiting examples of protecting groups include the following: carbobenzyloxy (Cbz), tert-Butyloxycarbonyl (Boc), p-methoxybenzyl carbonyl (Moz), 9-fluorenylmethyloxycarbonyl (FMOC), acetyl (Ac), benzoyl (Bz), benzyl (Bn), carbamates, p-methoxybenzyl (Pmb), 3,4-dimethoxybenzyl (Dmpm), p-methoxyphenyl (Pmp), tosyl (Ts), and trichloroethyl chloroformate (Troc).

In some embodiments, the chiral substituent precursor is (S)-camphor sulfonyl chloride, or (R)-menthyl chloroformate.

The unsubstituted atropisomer generally may be any unsubstituted atropisomer capable of reacting with the chiral substituent precursor, as described herein. In some embodiments, the unsubstituted atropisomer includes a compound of formula (I'), (II'), (III'), or (IV'):

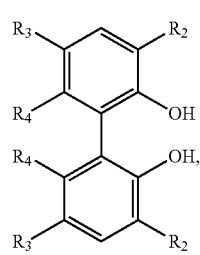

(I')

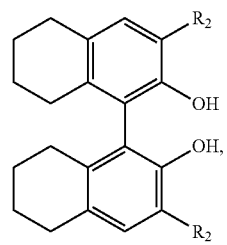

(II')

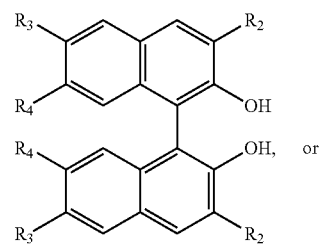

(III')

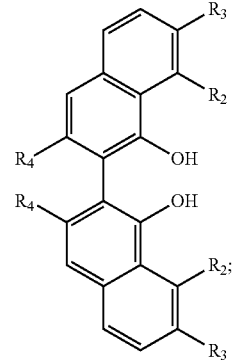

(IV')

wherein (i) $R_2$ is independently selected from hydrogen, a $C_1$-$C_{30}$ hydrocarbyl, or a halogen, (ii) $R_3$ is independently selected from hydrogen, a $C_1$-$C_{30}$ hydrocarbyl, or a halogen, and (iii) $R_4$ is independently selected from hydrogen or a halogen.

In some embodiments, the unsubstituted atropisomer is a compound of formula (I'), (II'), (III'), and (IV'), wherein $R_2$ is independently selected from the following substituents:

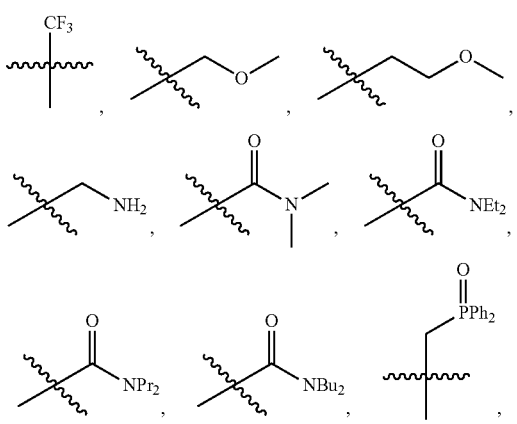

-continued
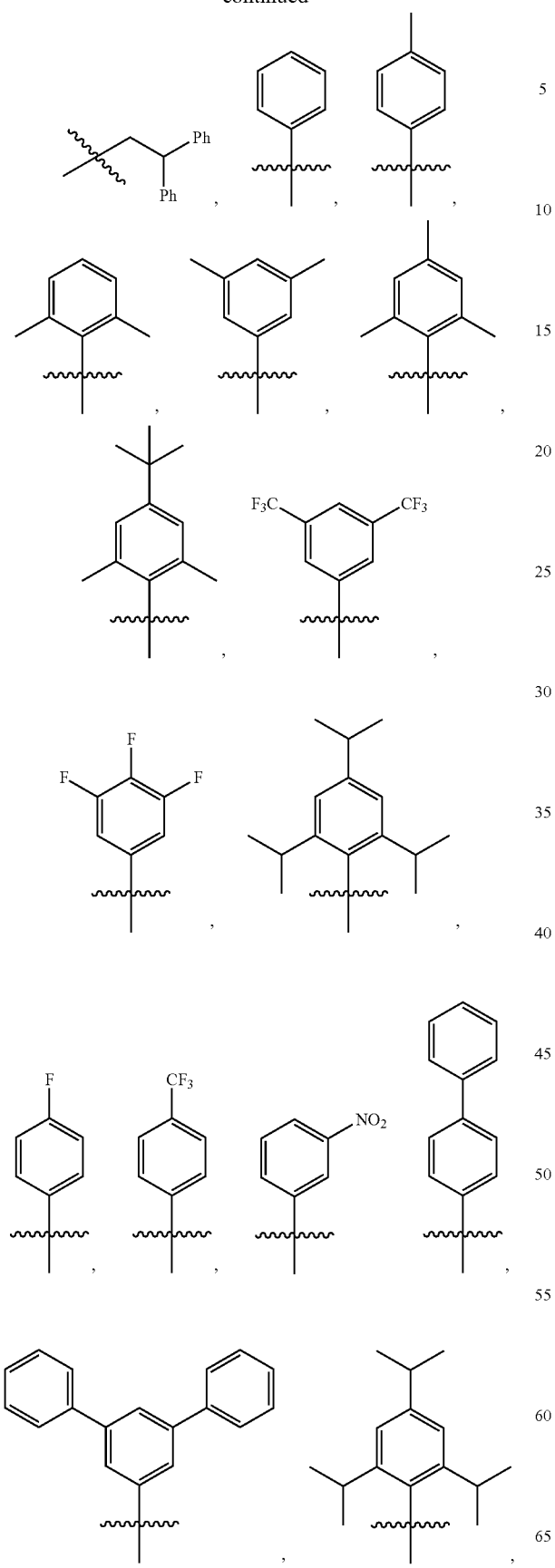
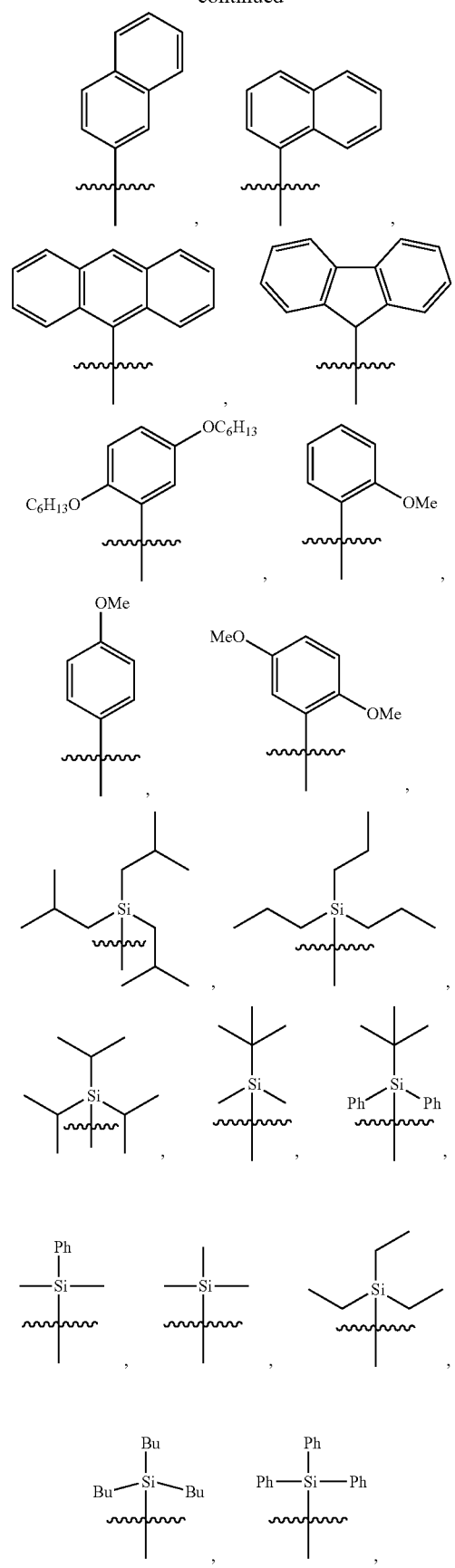

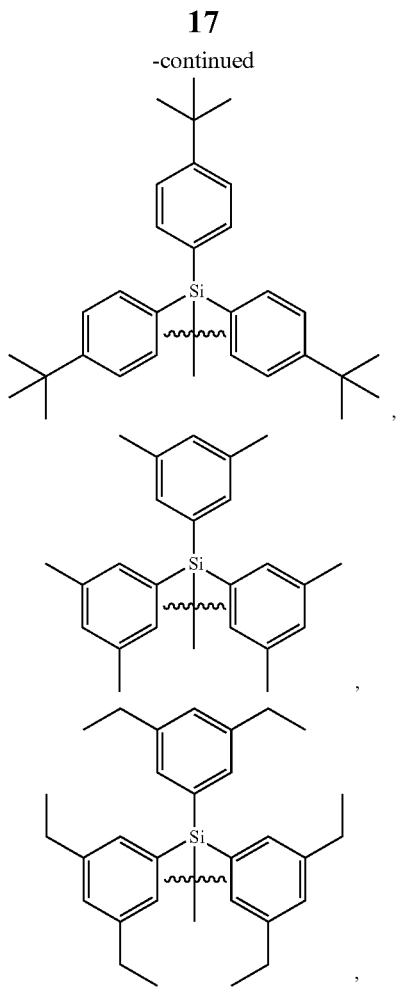
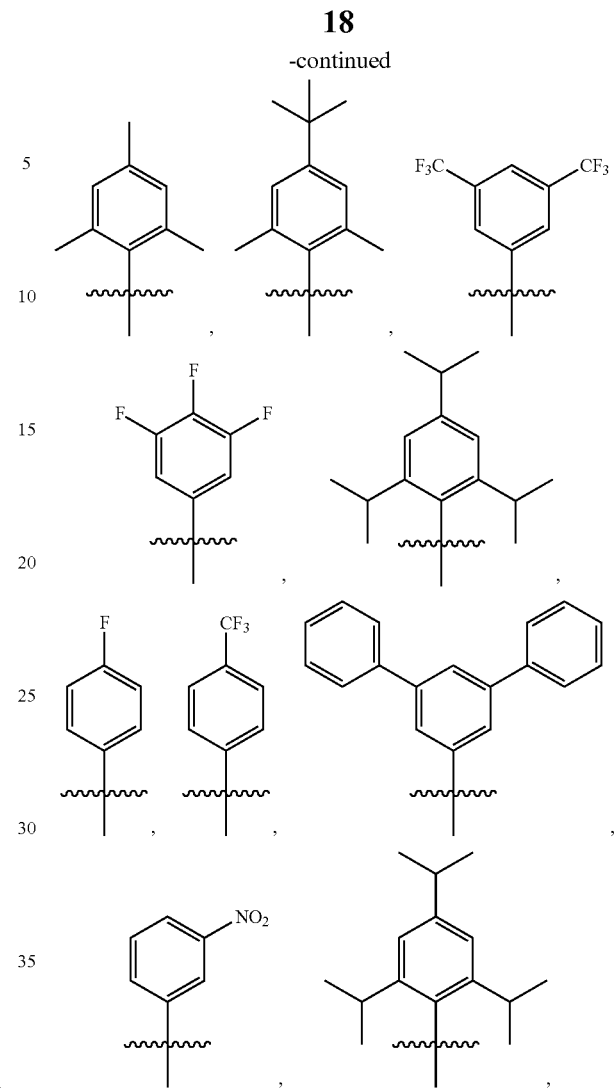
4-β-naphthylphenyl, 4-t-BuC$_6$H$_4$, or 3,5-t-Bu$_2$C$_6$H$_3$.
In some embodiments, the unsubstituted atropisomer is a compound of formula (I'), (II'), (III'), and (IV'), wherein R$_3$ is independently selected from the following substituents:
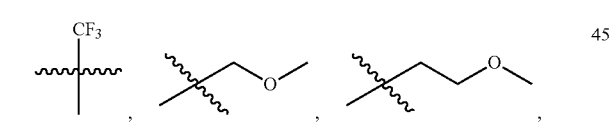
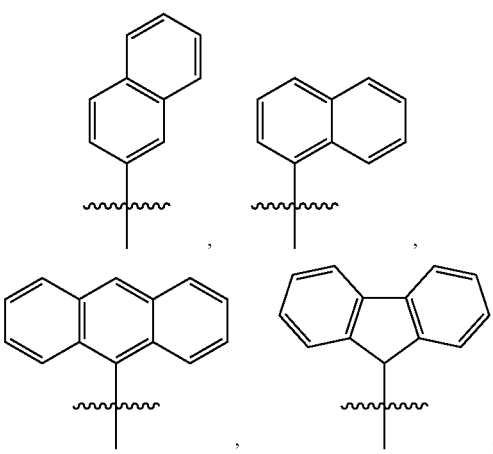
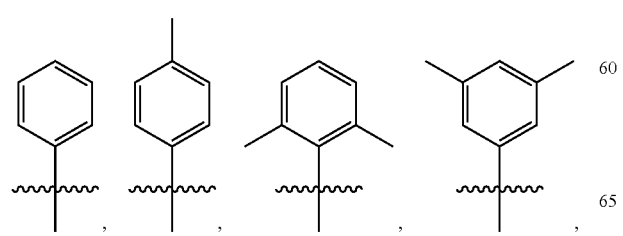
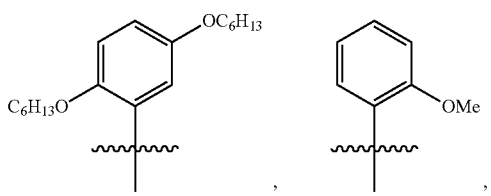

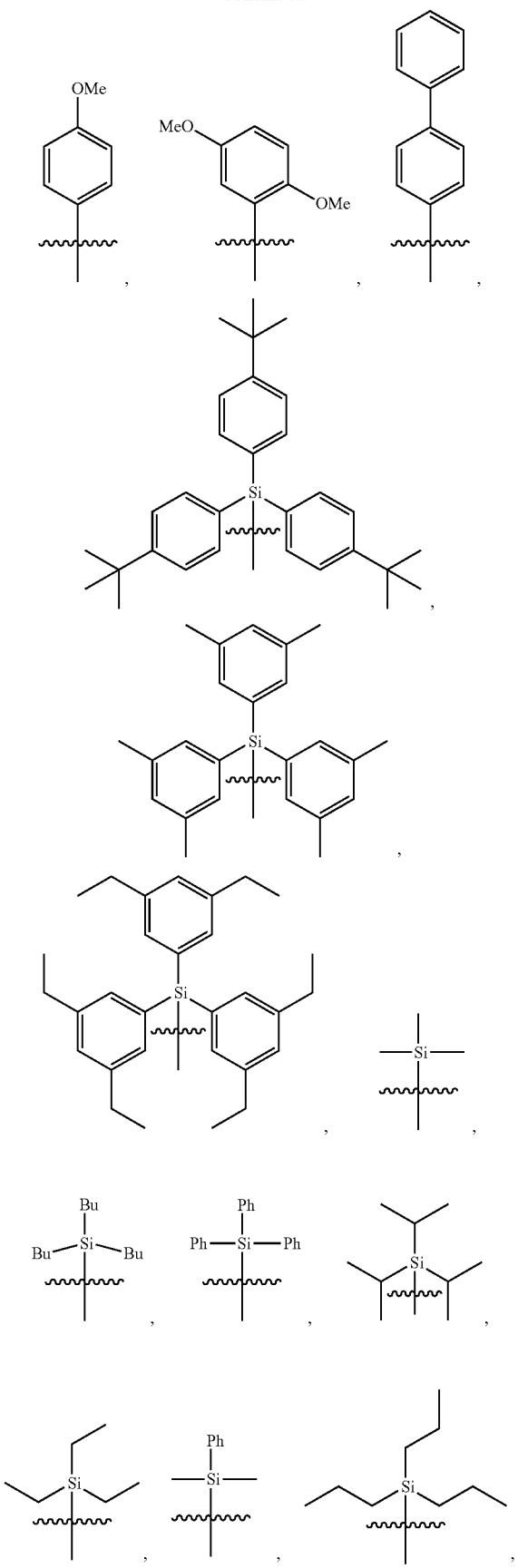

,

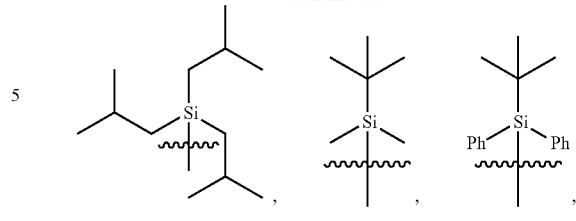

,

4-β-naphthylphenyl, 4-t-BuC$_6$H$_4$, or 3,5-t-Bu$_2$C$_6$H$_3$.

Generally, the unsubstituted atropisomer and the chiral substituent precursor may be contacted in the presence of any liquid and under any conditions. In some embodiments, an unsubstituted atropisomer and a chiral substituent precursor are contacted in the presence of dichloromethane. In some embodiments, an unsubstituted atropisomer and a chiral substituent precursor are contacted under nitrogen gas. In some embodiments, an unsubstituted atropisomer and a chiral substituent precursor are contacted in the presence of dichloromethane and under nitrogen gas. The liquid in which an unsubstituted atropisomer and a chiral substituent precursor are contacted may be the same as, or different than, a liquid in which the resulting atropisomer is irradiated.

Generally, any liquid, including those in which the reactants and/or products are at least partially soluble may be used in the methods provided herein. The liquid can include a polar solvent, a non-polar solvent, a protic solvent, an aprotic solvent, a chiral solvent, etc. The liquid may include a non-polar solvent, or a combination of two or more non-polar solvents. Non-limiting examples of liquids include toluene, acetonitrile, hexanes, acetone, ethanol, dichloromethane, or any combination thereof. In one embodiment, the liquid includes a chiral solvent, such as (−)-ethyl L-lactate, (R)-(+)-limonene, (S)-(−)-limonene, (−)-β-pinene, (R)-(−)-3,3-dimethyl-2-butylamine, (S)-(+)-1-cyclohexylethylamine. Not wishing to be bound by any particular theory, it is believed that a chiral solvent may be used to tailor an enantiomeric excess achieved by the methods provided herein.

Generally, an atropisomer may be irradiated with any electromagnetic radiation that includes one or more wavelengths capable of altering the enantiomeric excess of the atropisomer. In some embodiments, irradiating an atropisomer includes exposing the atropisomer to electromagnetic radiation including one or more wavelengths of about 10 nm to about 900 nm, about 200 nm to about 900 nm, about 200 nm to about 800 nm, or about 200 nm to about 400 nm. For example, an atropisomer may be exposed to electromagnetic radiation having a wavelength of about 365 nm. In some embodiments, the atropisomer is in a liquid for at least part of the irradiating.

In some embodiments, an atropisomer is contacted with a base during at least a portion of the irradiating of the atropisomer. In some embodiments, the base is a base that includes a nitrogen atom. In some embodiments, the base is triethylamine.

An atropisomer may be irradiated for a time sufficient to achieve a desired enantiomeric excess. An atropisomer may be irradiated for about 1 to about 60 minutes, about 1 to about 40 minutes, about 5 to about 30 minutes, about 10 to about 30 minutes, or about 20 minutes. Other times are envisioned, however.

In some embodiments, the methods provided herein also include removing the at least one chiral substituent. In some embodiments, the at least one chiral substituent may be removed by contacting the atropisomer with another reactant, such as an acid.

Also provided herein are atropisomers. In some embodiments, the atropisomers include an atropisomer according to formula (I), (II), (III), or (IV):

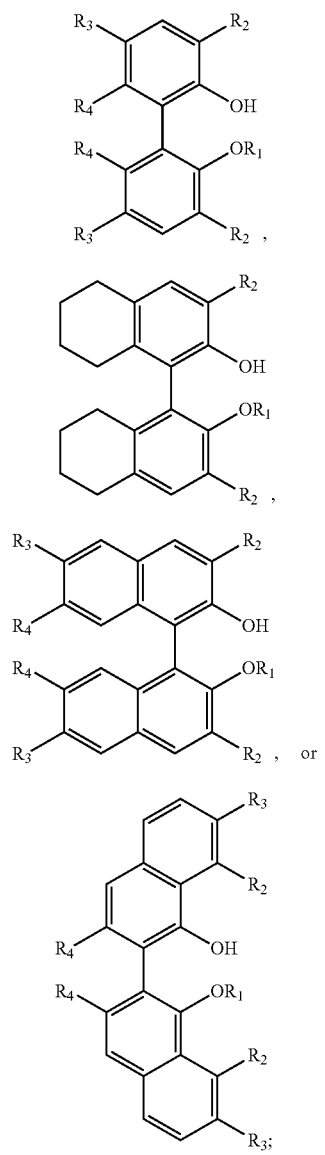

wherein (i) $R_1$ is a $C_1$-$C_{30}$ hydrocarbyl comprising at least one chiral atom, (ii) $R_2$ is independently selected from hydrogen, a $C_1$-$C_{30}$ hydrocarbyl, or a halogen, (iii) $R_3$ is independently selected from hydrogen, a $C_1$-$C_{30}$ hydrocarbyl, or a halogen, and (iv) $R_4$ is independently selected from hydrogen or a halogen.

In some embodiments, the atropisomers include an atropisomer according to formula (I), (II), (III), or (IV), wherein $R_1$ is an N-protected amino acid substituent.

In some embodiments, the atropisomers include an atropisomer according to formula (I), (II), (III), or (IV), wherein (i) $R_2$ is independently selected from the following substituents—

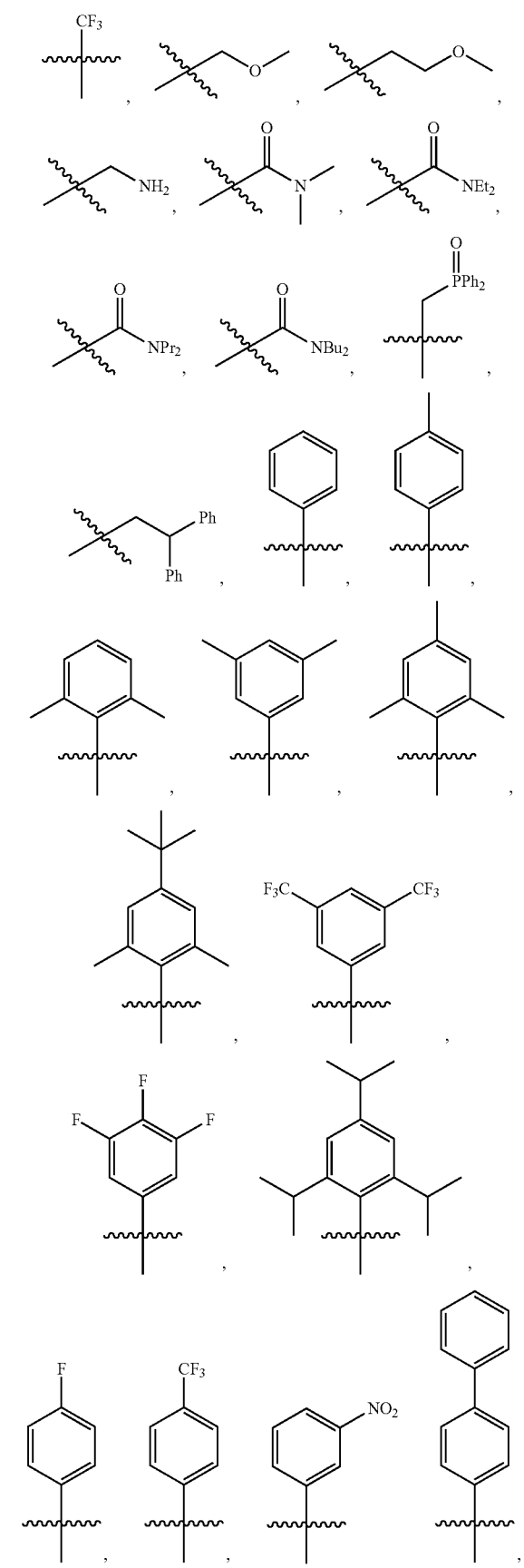

-continued
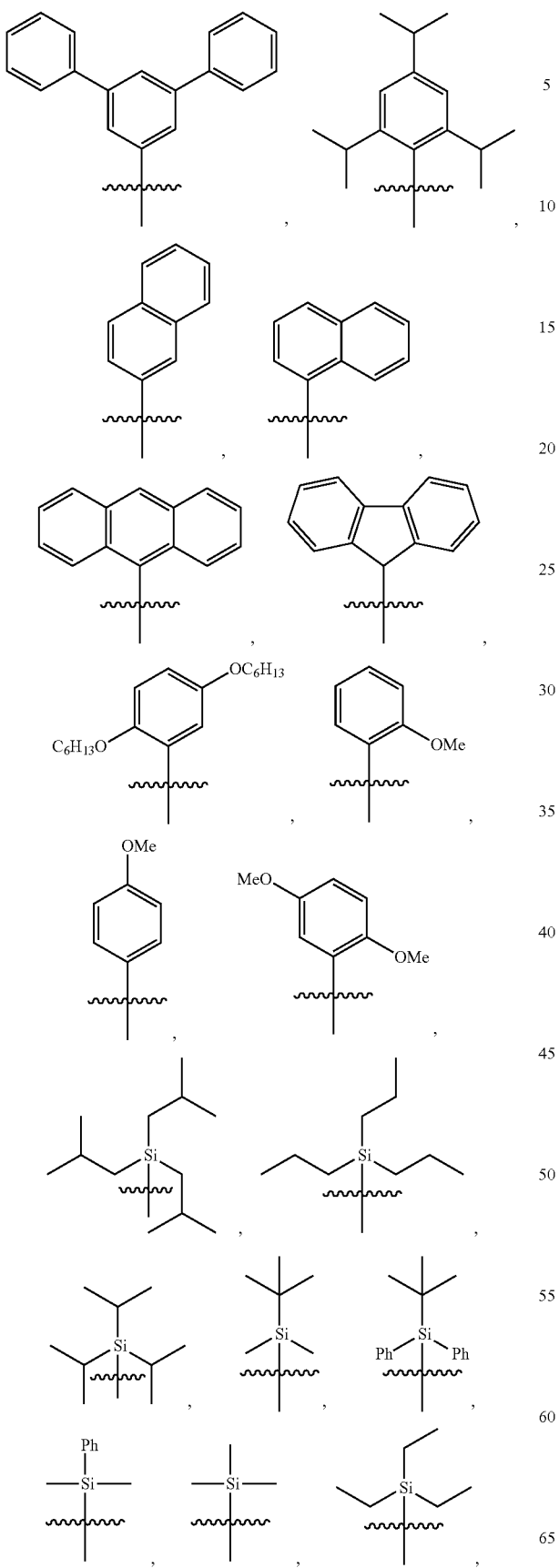
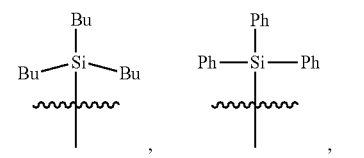
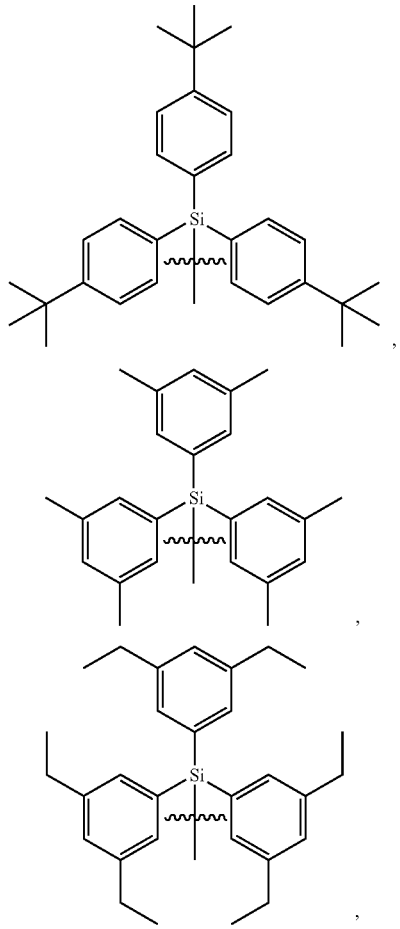
4-β-naphthylphenyl, 4-t-BuC$_6$H$_4$, or 3,5-t-Bu$_2$C$_6$H$_3$.
In some embodiments, the atropisomers include an atropisomer according to formula (I), (II), (III), or (IV), wherein R$_3$ is independently selected from the following substituents—
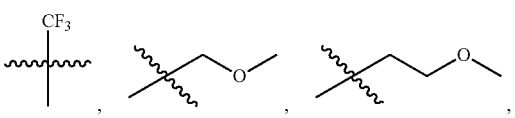
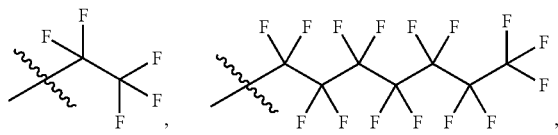

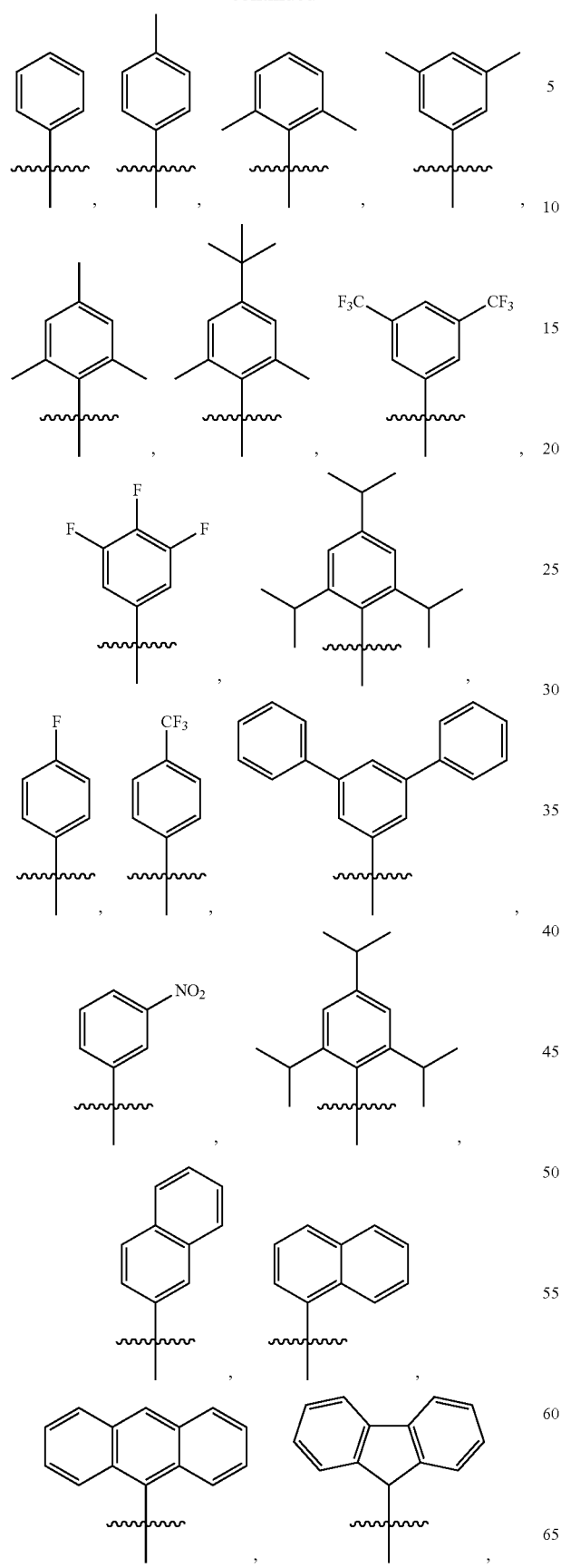
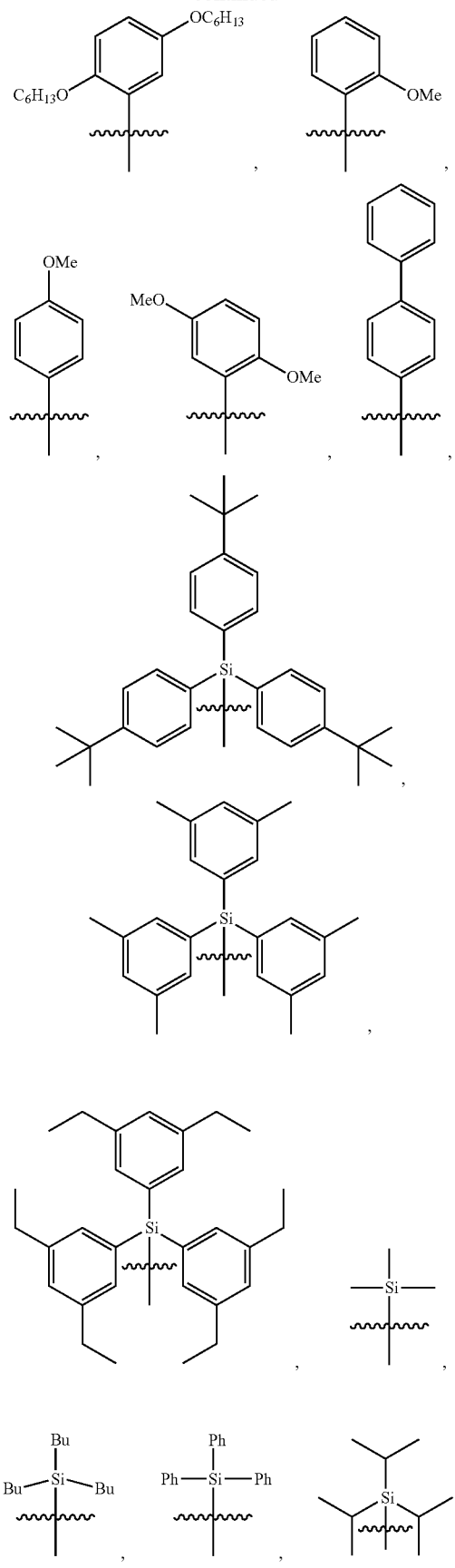

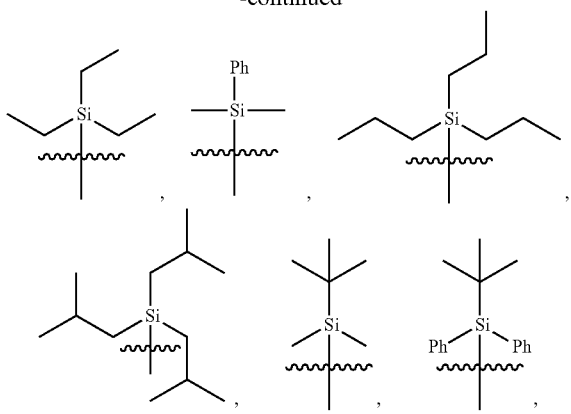

4-β-naphthylphenyl, 4-t-BuC$_6$H$_4$, or 3,5-t-Bu$_2$C$_6$H$_3$.

The phrase "C$_1$-C$_{30}$ hydrocarbyl," as used herein, generally refers to an aliphatic group, an aromatic or aryl group, a cyclic group, or any combination thereof; any substituted derivative thereof, including but not limited to any halide-, alkoxide-, or amide-substituted derivative thereof; or hydrogen. Also included in the definition of the C$_1$-C$_{30}$ hydrocarbyl are any unsubstituted, branched, or linear analogs thereof. The C$_1$-C$_{30}$ hydrocarbyl may be substituted with one or more functional moieties selected from a halide, an ether, a ketone, an ester, an amide, a nitrile, a heterocycle comprising at least one N-, O-, or S-heteroatom, an aldehyde, a thioether, an imine, a sulfone, a carbonate, a urethane, a urea, or an imide. The C$_1$-C$_{30}$ hydrocarbyl also may include one or more silicon atoms.

Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from 1 to about 30 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Examples of aryl or aromatic moieties include, but are not limited to, anthracenyl, azulenyl, biphenyl, fluorenyl, indan, indenyl, naphthyl, phenanthrenyl, phenyl, 1,2,3,4-tetrahydro-naphthalene, and the like, including substituted derivatives thereof, in each instance having from 3 to 30 carbons. Substituted derivatives of aromatic compounds include, but are not limited to, tolyl, xylyl, mesityl, and the like, including any heteroatom substituted derivative thereof. Examples of cyclic groups, in each instance, include, but are not limited to, cycloparaffins, cycloolefins, cycloacetylenes, arenes such as phenyl, bicyclic groups and the like, including substituted derivatives thereof, in each instance having from about 3 to about 30 carbon atoms. Thus heteroatom-substituted cyclic groups such as furanyl are also included herein.

In each instance, aliphatic and cyclic groups are groups comprising an aliphatic portion and a cyclic portion, examples of which include, but are not limited to, groups such as: —(CH$_2$)$_m$C$_6$H$_q$M$_{5-q}$ wherein m is an integer from 1 to about 10, q is an integer from 1 to 5, inclusive; (CH$_2$)$_m$C$_6$H$_q$R$_{10-q}$ wherein m is an integer from 1 to about 10, q is an integer from 1 to 10, inclusive; and (CH$_2$)$_m$C$_5$H$_q$R$_{9-q}$ wherein m is an integer from 1 to about 10, q is an integer from 1 to 9, inclusive. In each instance and as defined above, M is independently selected from: an aliphatic group; an aromatic group; a cyclic group; any combination thereof; any substituted derivative thereof, including but not limited to any halide-, alkoxide-, or amide-substituted derivative thereof; any one of which has from 1 to about 30 carbon atoms; or hydrogen. In one aspect, aliphatic and cyclic groups include, but are not limited to: —CH$_2$C$_6$H$_5$; —CH$_2$C$_6$H$_4$F; —CH$_2$C$_6$H$_4$Cl; —CH$_2$C$_6$H$_4$Br; —CH$_2$C$_6$H$_4$I; —CH$_2$C$_6$H$_4$OMe; —CH$_2$C$_6$H$_4$OEt; —CH$_2$C$_6$H$_4$NH$_2$; —CH$_2$C$_6$H$_4$NMe$_2$; —CH$_2$C$_6$H$_4$NEt$_2$; —CH$_2$CH$_2$C$_6$H$_5$; —CH$_2$CH$_2$C$_6$H$_4$F; —CH$_2$CH$_2$C$_6$H$_4$Cl; —CH$_2$CH$_2$C$_6$H$_4$Br; —CH$_2$CH$_2$C$_6$H$_4$I; —CH$_2$CH$_2$C$_6$H$_4$OMe; —CH$_2$CH$_2$C$_6$H$_4$OEt; —CH$_2$CH$_2$C$_6$H$_4$NH$_2$; —CH$_2$CH$_2$C$_6$H$_4$NMe$_2$; —CH$_2$CH$_2$C$_6$H$_4$NEt$_2$; any regioisomer thereof, or any substituted derivative thereof. Thus, a cyclic group refers to groups such as C$_6$H$_q$M$_{5-q}$, C$_6$H$_q$R$_{10-q}$, C$_5$H$_q$R$_{9-q}$, and the like, where q, M, and R are defined immediately above.

In each instance, the heterocycle comprising at least one N-, O-, or S-heteroatom may be selected from the group consisting of: morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyi, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, or benzothiopyranyl S,S-dioxide.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O— alkyl- or —OC(O) NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

In the descriptions provided herein, the terms "includes," "is," "containing," "having," and "comprises" are used in an open-ended fashion, and thus should be interpreted to mean "including, but not limited to." When structures or methods are claimed or described in terms of "comprising" various components or processing features, the structures and methods can also "consist essentially of" or "consist of" the various components or processing features, unless stated otherwise.

The terms "a," "an," and "the" are intended to include plural alternatives, e.g., at least one. For instance, the disclosure of "an atropisomer," "at least one chiral substituent," and the like, is meant to encompass one, or mixtures or combinations of more than one atropisomer, chiral substituents, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, that "the enantiomeric excess is about 95% to 100% prior to the irradiating of the atropisomer." This range should be interpreted as encompassing values in a range of about 95% to 100%, and further encompasses "about" each of 96%, 97%, 98%, and 99%, including any ranges and sub-ranges between any of these values.

The processes described herein may be carried out or performed in any suitable order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—BINOL—Camphor Sulfonyl Coupling

To a flame-dried 50 mL 3-neck flask was added 0.35 mmol of (S)-camphor sulfonyl chloride. The flask was evacuated and backfilled with $N_2$ three times and submerged in an ice bath.

5 mL of a 0.07 M solution of racemic [1,1'-binaphthalene]-2,2'-diol (BINOL) (0.35 mmol) in anhydrous dichloromethane (DCM) was cooled to 0° C. in an ice bath and added via syringe to the flask under positive $N_2$ pressure.

0.121 mL of anhydrous trimethylamine (TEA) was then added to the reaction flask.

The mixture was stirred under $N_2$ and allowed to return to room temperature over 12 hours. The reaction was quenched with 5 mL of $H_2O$, stirred for 15 minutes, and extracted three times with DCM. The organic layer was then washed with brine, and dried over $Na_2SO_4$.

Liquid was removed under vacuum to yield a yellow waxy solid.

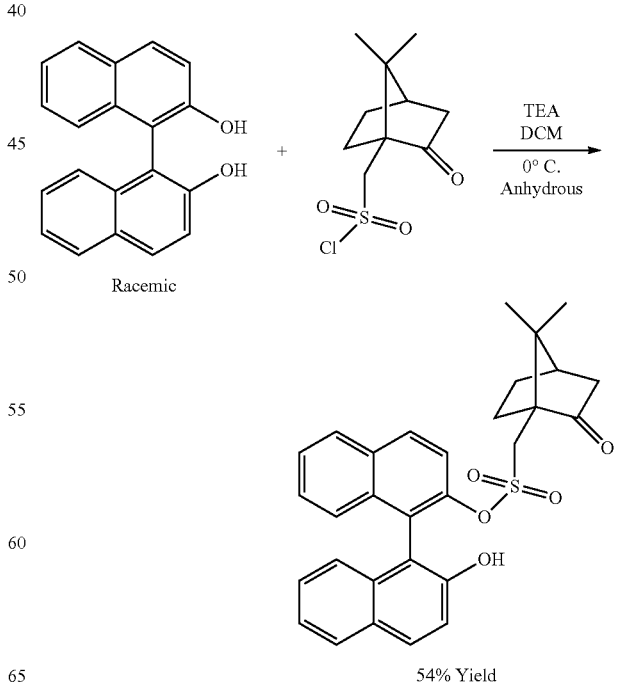

A silica column was prepared using 12 g of 400-600 mesh silica, wet packed with hexanes. The crude product was dissolved in 0.5 mL of DCM, and wet loaded onto the column.

The product was eluted with 20% ethylacetate in hexanes. Liquid was evaporated under vacuum to yield monosubstituted camphor sulfonyl BINOL (54% yield).

Example 2—BINOL—Menthyl Carbonate Coupling

To a flame-dried 50 mL 3-neck flask was added 0.35 mmol of (R)-menthyl chloroformate. The flask was evacuated and backfilled with $N_2$ three times, and submerged in an ice bath.

5 mL of a 0.07 M solution of racemic BINOL (0.35 mmol) in anhydrous dichloromethane (DCM) was cooled to 0° C. in an ice bath, and added via syringe to the flask under positive $N_2$ pressure.

0.121 mL of TEA was then added to the reaction flask. The mixture was stirred under $N_2$ and allowed to return to room temperature over 3 hours.

The reaction was quenched with 5 mL of 1M HCl, stirred for 15 minutes, and extracted three times with DCM. The organic layer was then washed with brine, and dried over $Na_2SO_4$.

Liquid was removed under vacuum to yield a pale waxy solid.

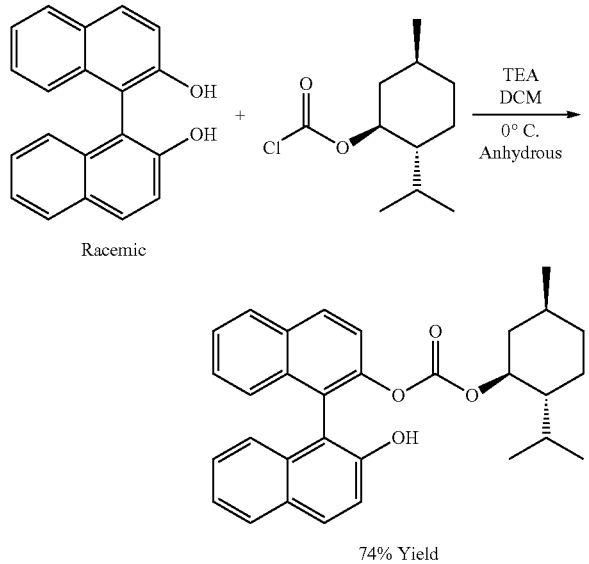

A silica column was prepared using 12 g of 400-600 mesh silica, wet packed with hexanes. The crude product was dissolved in 0.5 mL of DCM, and wet loaded onto the column. The product was eluted with 10% ethylacetate in hexanes.

Liquid was evaporated under vacuum to yield monosubstituted menthyl carbonate BINOL (74% yield).

Example 3—BINOL—Amino Acid Coupling

To a flame-dried 50 mL 3-neck flask was added 0.35 mmol of N-protected amino acid, 0.35 mmol of dicyclohexylcarboimide (DCC), and 0.035 mmol of N,N-dimethylpyridin-4-amine (DMAP). The flask was evacuated and backfilled with $N_2$ three times, and submerged in an ice bath.

5 mL of a 0.07 M solution of racemic BINOL (0.35 mmol) in anhydrous dichloromethane (DCM) was cooled to 0° C. in an ice bath, and added to the flask under positive $N_2$ pressure.

The mixture was removed from the ice bath, and allowed to return to room temperature while stirring. Reaction progress was monitored by TLC until completion, which took about 2 to about 3 hours. The reaction mixture was filtered through a fine glass frit to remove the precipitate, which was then washed with three 1 mL portions of cold DCM.

The resulting filtrate was dried under vacuum to yield a white flakey solid.

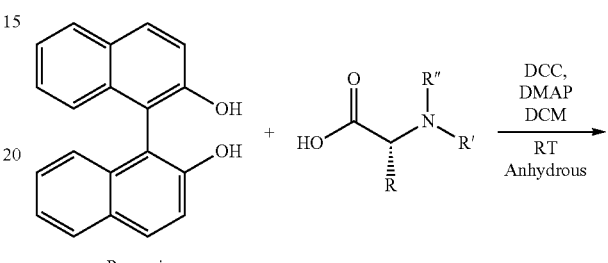

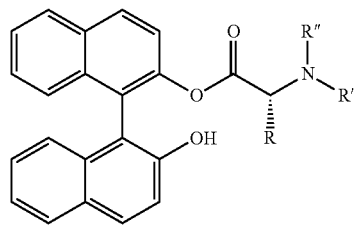

A silica column was prepared using 12 g of 400-600 mesh silica, wet packed with hexanes. The crude product was dissolved in 0.5 mL of DCM, and wet loaded onto the column.

The product was eluted with 25% ethylacetate in hexanes. Liquid was evaporated under vacuum to yield monosubstituted amino acid BINOL.

The yields corresponding to the various amino acids, and the structures of the protecting groups are provided in the following table:

| Protected Amino Acid | Yield (%) | Protecting Groups |
|---|---|---|
| Boc-Phg-OH | 72 | Boc- |
| Boc-Phe-OH | 75 | Cbz- |

| Protected Amino Acid | Yield (%) | Protecting Groups |
|---|---|---|
| Boc-Pro-OH | 84 | |
| Boc-Trp-OH | 67 | |
| Cbz-Trp-OH | 62 | |
| Cbz-Pro-OH | 78 | |

Example 4—Photoisomerization Reaction Procedure

The products of Examples 1-3 may be photoisomerized according to any of the embodiments described herein, including the procedure of this example.

In this example, the product of Example 1 (i.e., racemic (S)-camphor-sulfonyl-BINOL) was subjected to photoisomerization by adding 0.25 mL of a 10 mM substituted BINOL solution in toluene, 0.7 5 mL of toluene, and 25 μL of TEA to a disposable glass culture tube.

The tube was stirred at room temperature, and irradiated with a 365 nm LED (M365L2-UV, fwhm=7.5 nm, THOR-LABS, USA) controlled by a LEDD1B T-Cube series LED driver (THORLABS, USA). After 20 minutes the reaction was stopped and dried under vacuum.

Figure 1A:
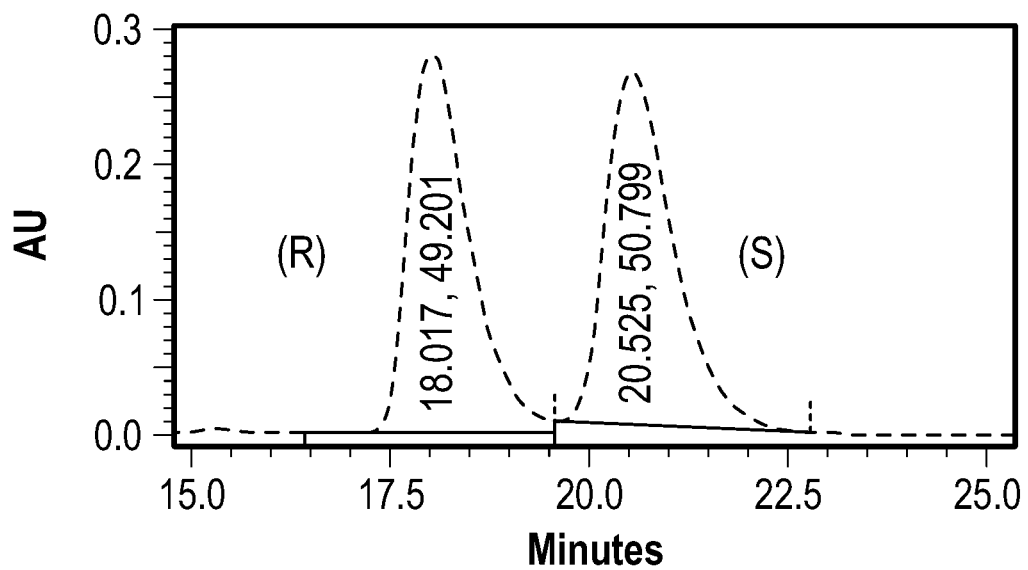
FIG. 1A depicts a chromatographic plot of one embodiment of a racemic atropisomer prior to irradiation.
Figure 1B:
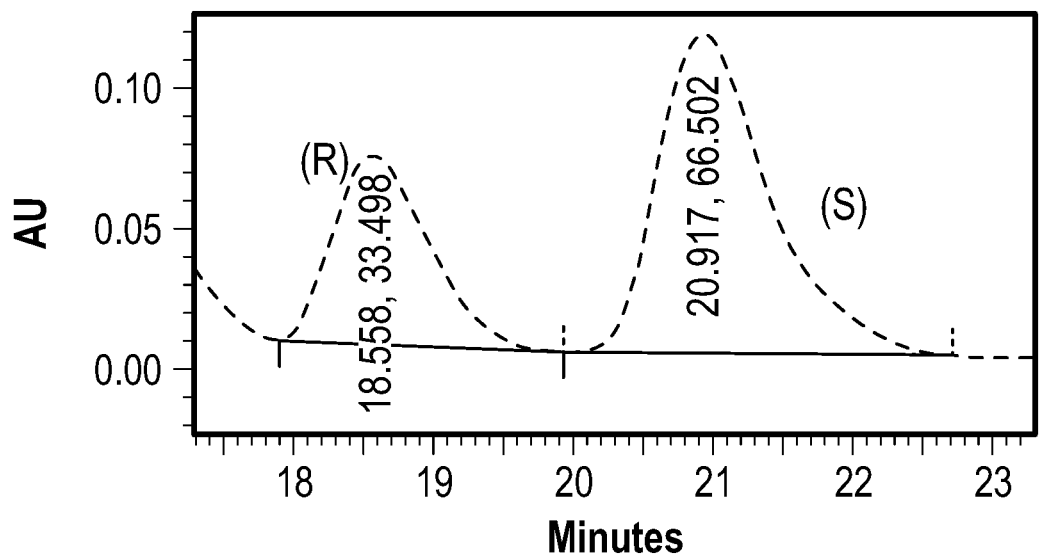
FIG. 1B depicts a chromatographic plot of the atropisomer of FIG. 1A after 20 minutes of irradiation.

The irradiation resulted in a 33% enantiomeric excess of the (S) isomer. This result is depicted at FIG. 1A and FIG. 1B. FIG. 1A depicts a chromatographic plot of racemic (S)-camphor-sulfonyl-BINOL prior to photoisomerization, and FIG. 1B depicts a chromatographic plot of the (S)-camphor-sulfonyl-BINOL after the photoisomerization process of this example.

Figure 2A:
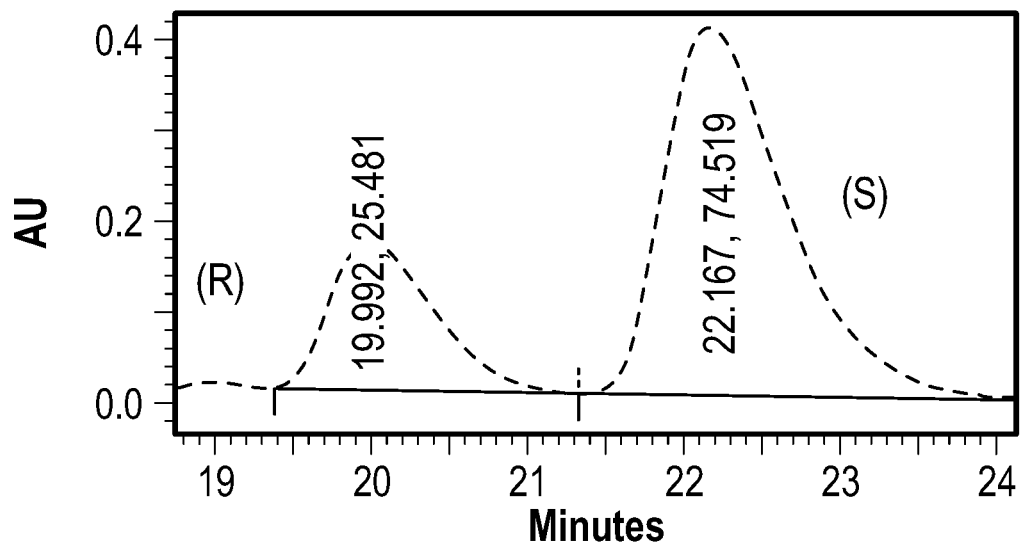
FIG. 2A depicts chromatographic data collected after one embodiment of an enantiopure atropisomer was irradiated for 10 minutes.
Figure 2B:
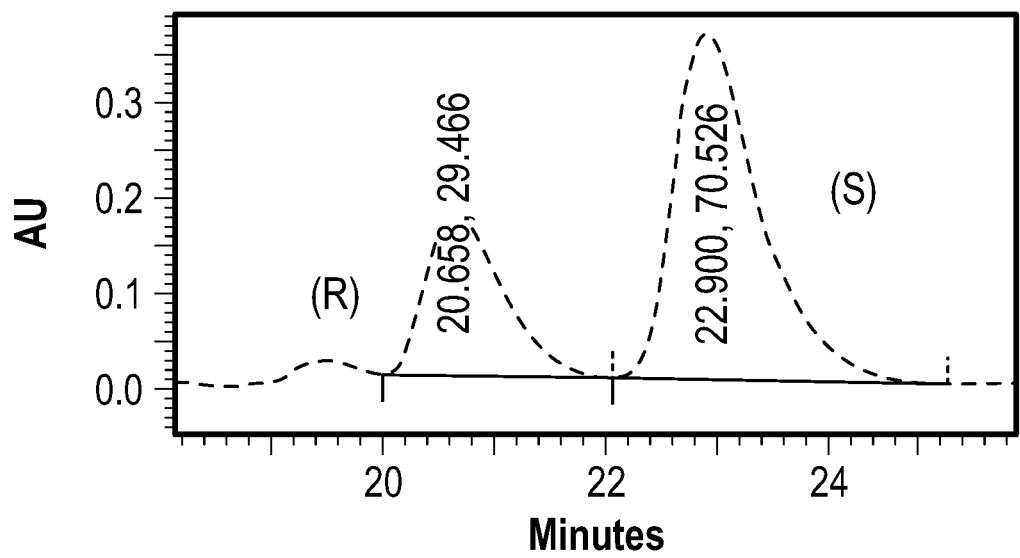
FIG. 2B depicts chromatographic data collected after one embodiment of an enantiopure atropisomer was irradiated for 20 minutes.

The photoisomerization process and chromatographic analysis of this example also was performed on enantiopure (S)-camphor-sulfonyl-BINOL. After 10 minutes of irradiation, a 50% enantiomeric excess of the (S)-camphor-sulfonyl-BINOL was observed, as depicted at FIG. 2A, and, after 20 minutes of irradiation, the enantiomeric excess of the (S)-camphor-sulfonyl-BINOL had been reduced to 40%, as depicted at FIG. 2B.

The photoisomerization process and chromatographic analysis of this example also was performed on a number of other racemic starting materials, including the product of Example 2. The products tested and the enantiomeric excess (EE) achieved by the photoisomerization process of this example are presented in the following table:

| Product | EE (%) |
|---|---|
| Menthyl Carbonate BINOL (Example 2) | 4 |
| Boc-Phg-BINOL | 63 |
| Cbz-Pro-BINOL | 25 |
| | 20 |

| Product | EE (%) |
| --- | --- |
| Boc-Ala-BINOL | 27 |
| Boc-Pro-BINOL | 7 |
| Boc-Trp-BINOL | 57 |
| Cbz-Trp-BINOL | |

Figure 3A:
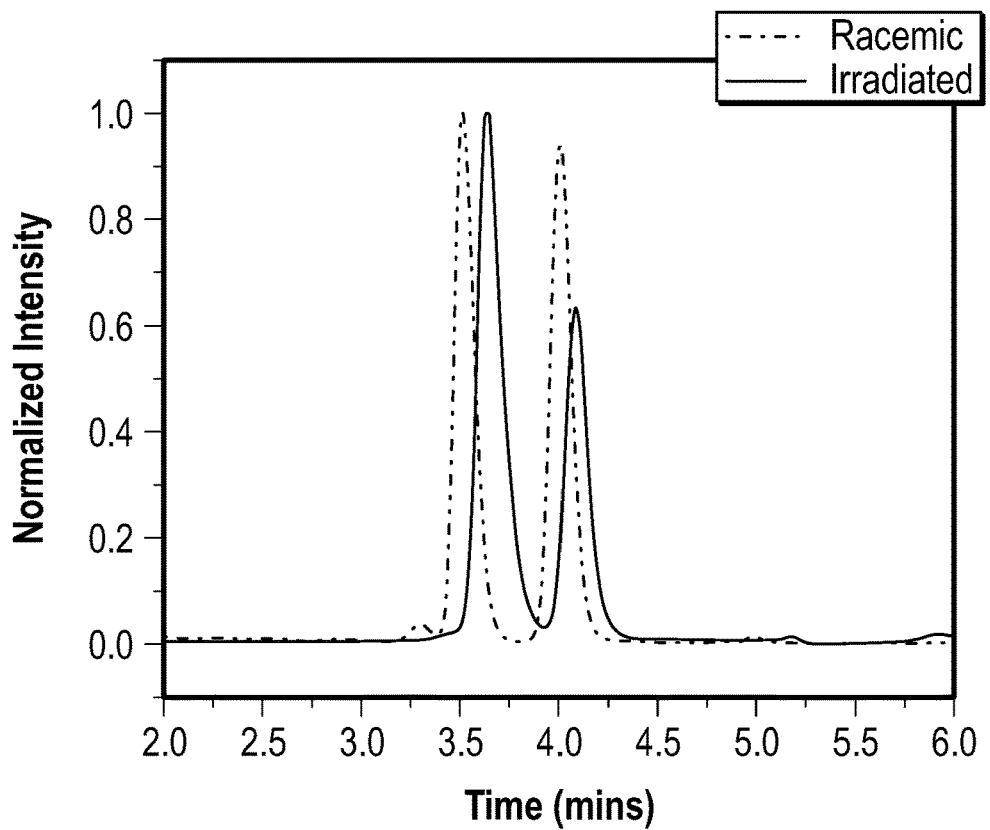
FIG. 3A depicts chromatographic data collected from one embodiment of a racemic atropisomer before and after 60 minutes of irradiation.
Figure 3B:
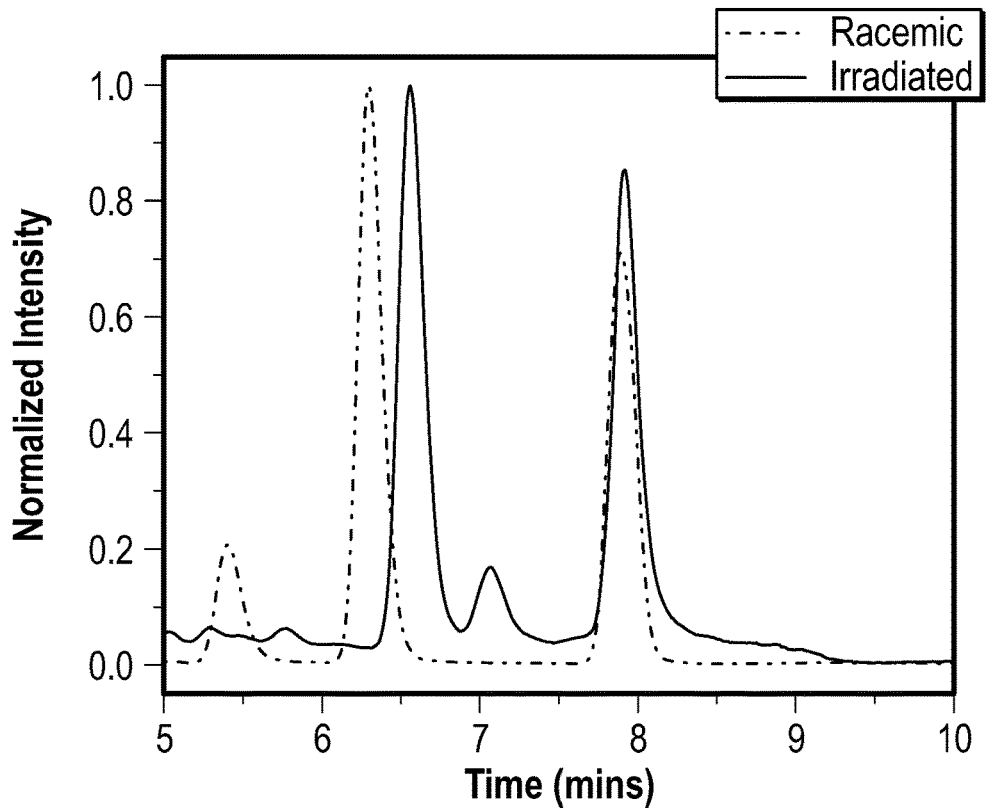
FIG. 3B depicts chromatographic data collected from one embodiment of a racemic atropisomer before and after 60 minutes of irradiation.
Figure 3C:
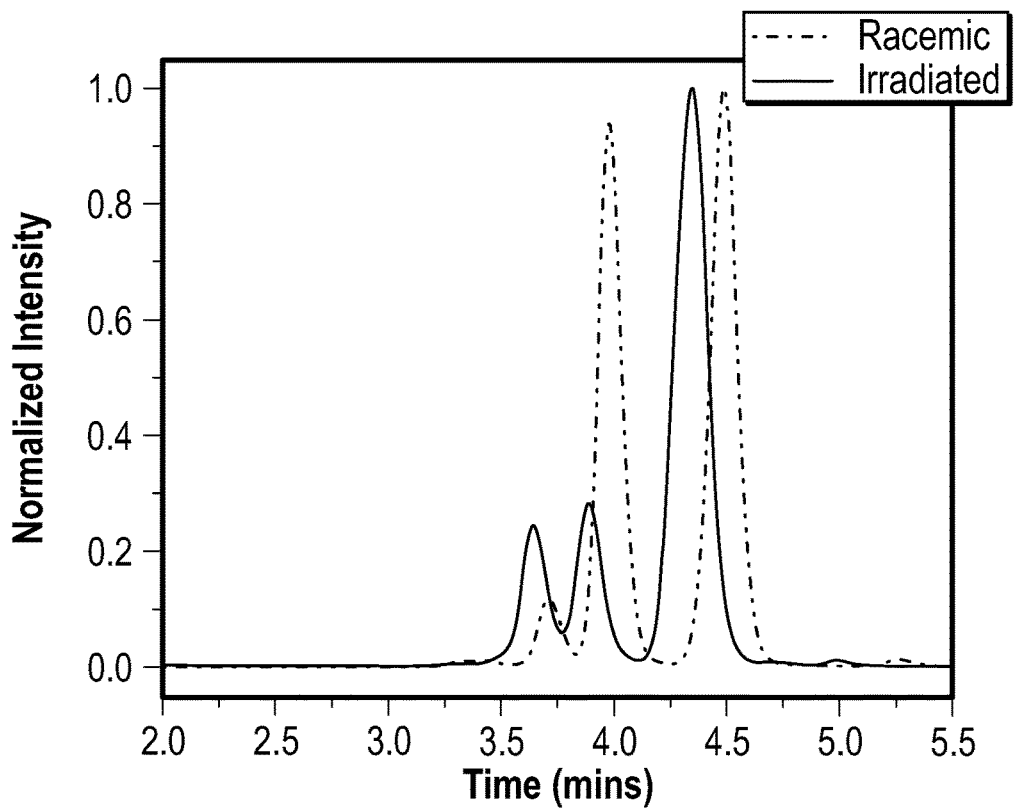
FIG. 3C depicts chromatographic data collected from one embodiment of a racemic atropisomer before and after 60 minutes of irradiation.
Figure 3D:
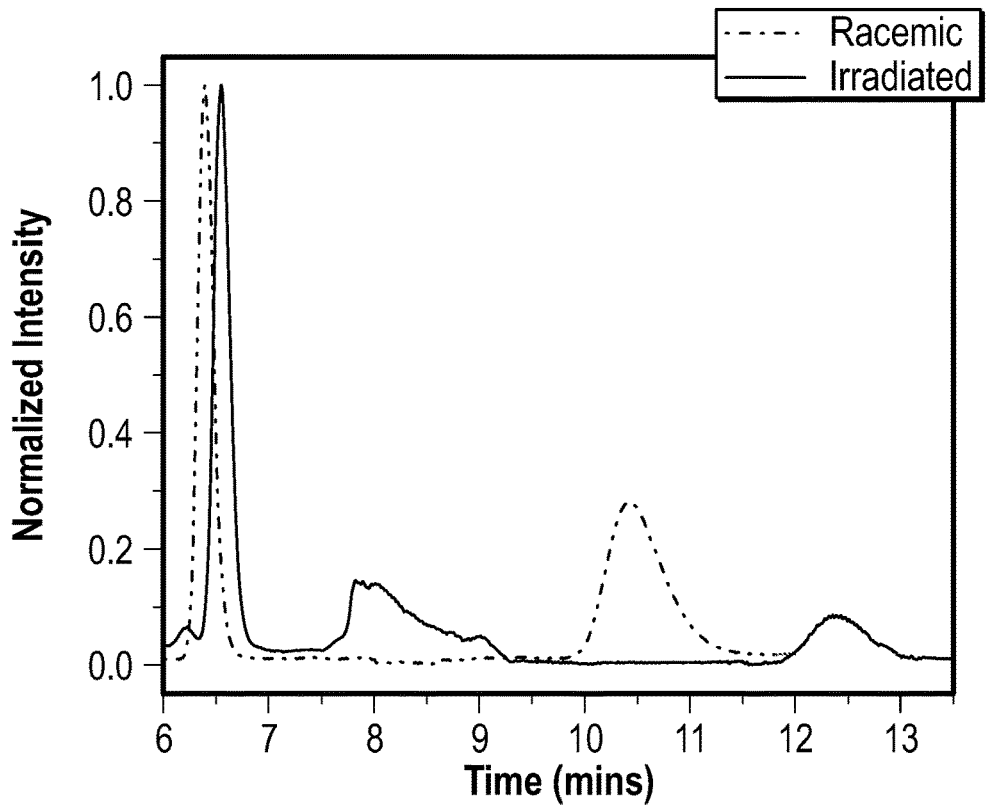
FIG. 3D depicts chromatographic data collected from one embodiment of a racemic atropisomer before and after 60 minutes of irradiation.
Figure 3E:
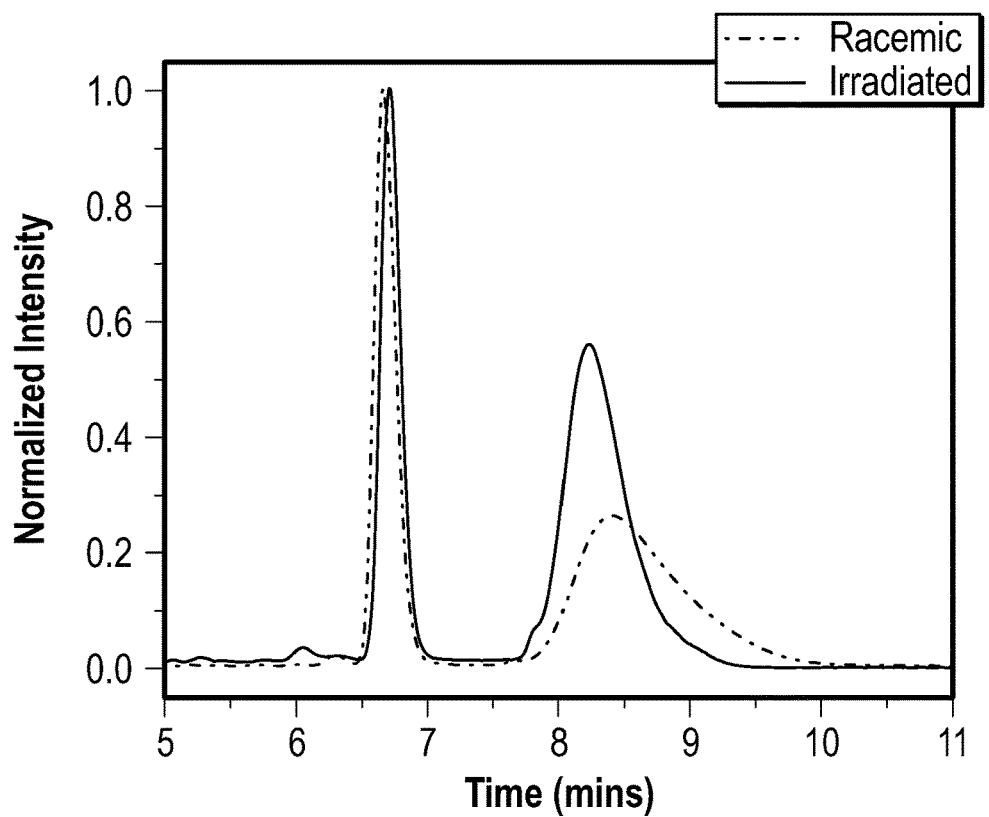
FIG. 3E depicts chromatographic data collected from one embodiment of a racemic atropisomer before and after 60 minutes of irradiation.
Figure 3F:
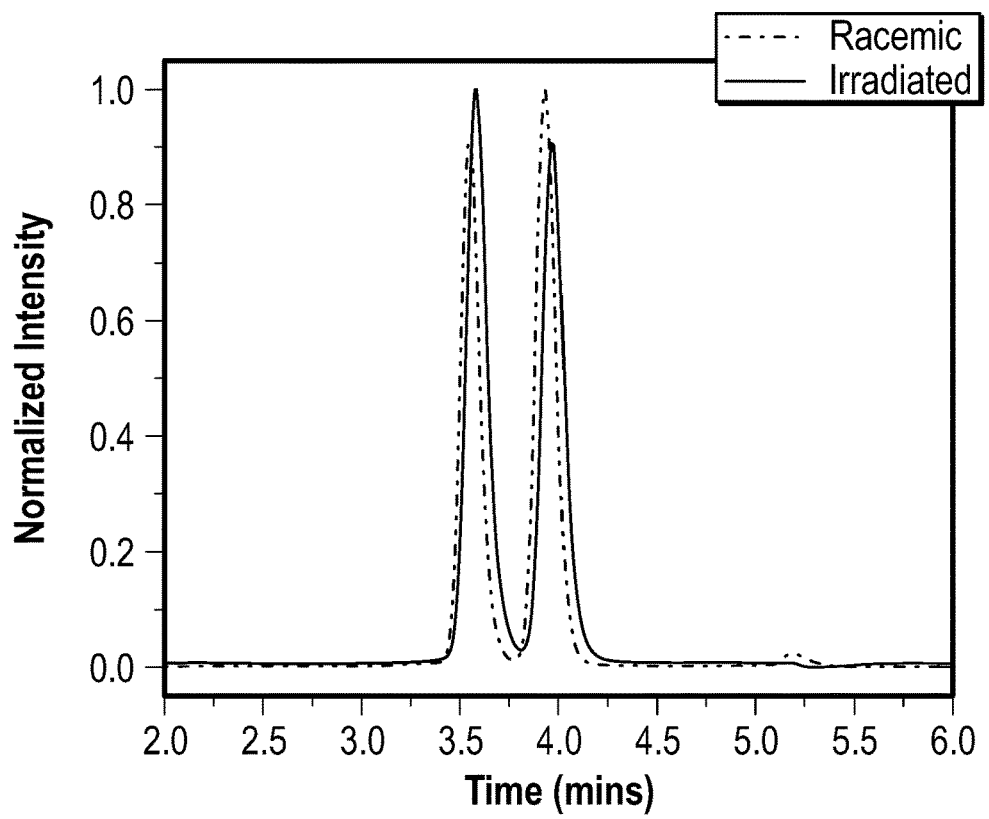
FIG. 3F depicts chromatographic data collected from one embodiment of a racemic atropisomer before and after 60 minutes of irradiation.
Figure 3G:
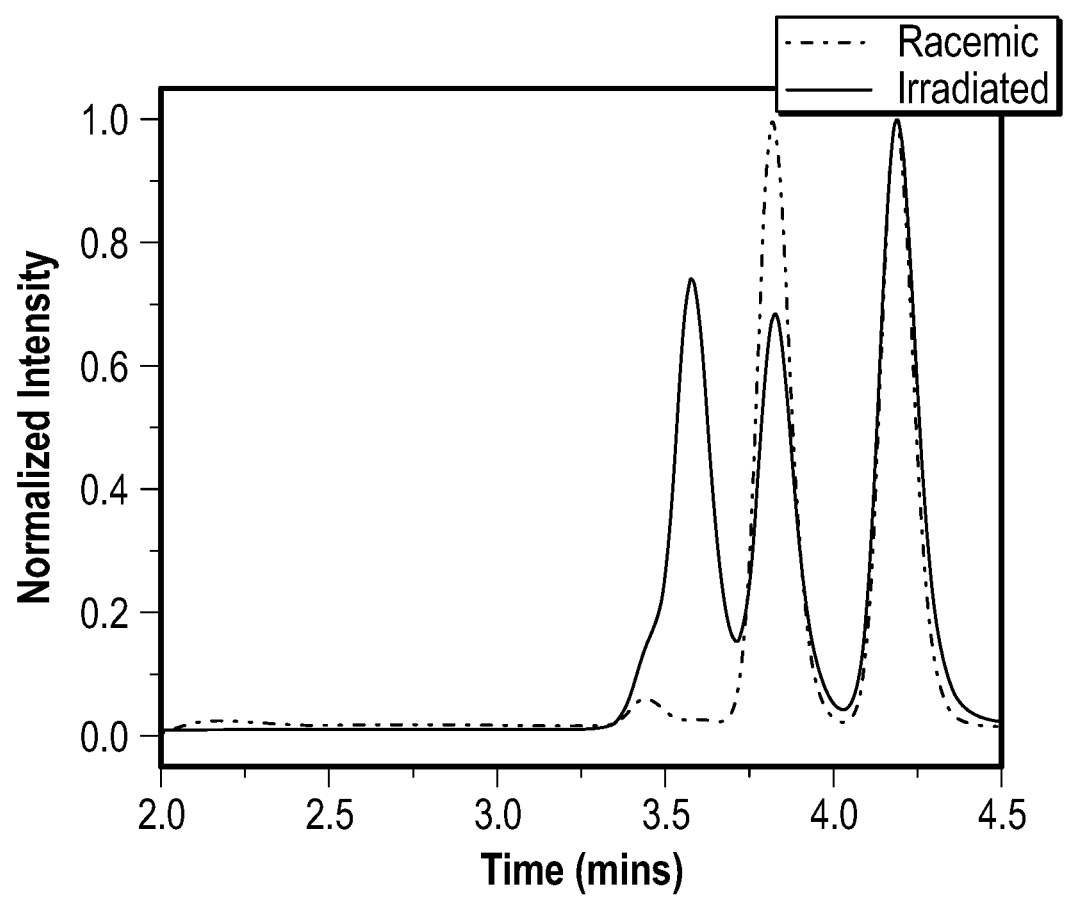
FIG. 3G depicts chromatographic data collected from one embodiment of a racemic atropisomer before and after 60 minutes of irradiation.

Super-critical fluid chromatography was used to determine the enantiomeric excess percentages of the foregoing table. The super-critical fluid chromatograph traces are depicted at FIG. 3A (Boc-Pro-BINOL), FIG. 3B (Boc-Trp-BINOL), FIG. 3C (Boc-Phg-BINOL), FIG. 3D (Cbz-Trp-BINOL), FIG. 3E (Cbz-Pro-BINOL), FIG. 3F (Menthyl-Carbonate-BINOL), and FIG. 3G (Boc-Ala-BINOL).

Example 5—Amino Acid Cleavage

Following the photoisomerization of an amino acid-substituted product, such as those of Example 3, the amino acid may be removed by the following cleaving procedure.

200 μL of methanol (MeOH) and 50 μL of 100 mM LiOH in MeOH was added to a test tube and stirred at room temperature for 30 minutes.

50 μL of 100 mM trifluoroacetic acid in MeOH added to test tube and stirred at room temperature for 5 minutes. The reaction mixture was dried under vacuum.

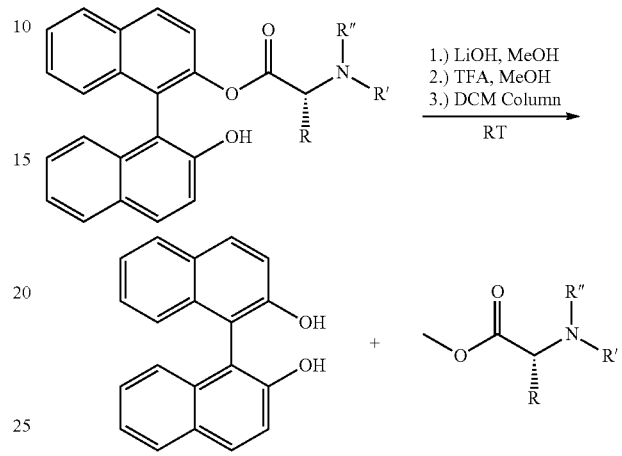

The crude product was dissolved in 0.5 mL of DCM, and wet loaded onto a 600 mg silica Pasteur pipette column. The product was eluted with DCM and dried under vacuum to yield BINOL as a white crystalline solid.

We claim:

1. A method of altering enantiomeric excess, the method comprising:

providing an atropisomer having an enantiomeric excess of 0% to 100%, wherein the atropisomer comprises at least one chiral substituent; and irradiating the atropisomer to alter the enantiomeric excess;

wherein the atropisomer comprises a compound of formula (I), (II), (III), or (IV)—

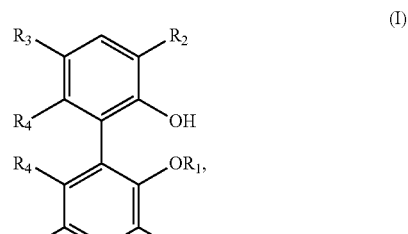

(I)

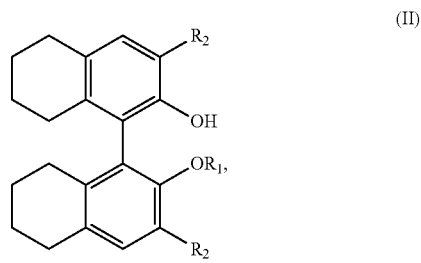

(II)

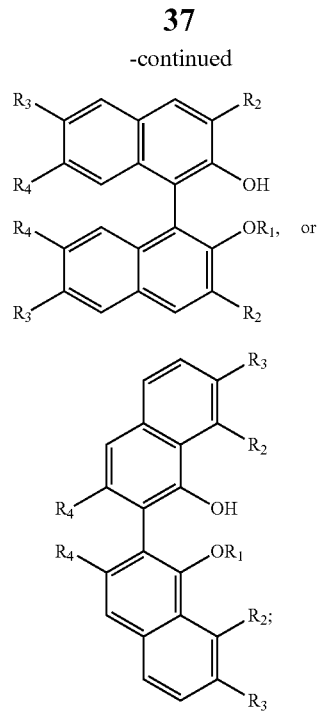

(III)

(IV)

wherein (i) $R_1$ is the at least one chiral substituent, (ii) $R_2$ is independently selected from hydrogen, a $C_1$-$C_{30}$ hydrocarbyl, or a halogen, (iii) $R_3$ is independently selected from hydrogen, a $C_1$-$C_{30}$ hydrocarbyl, or a halogen, and (iv) $R_4$ is independently selected from hydrogen or a halogen.

2. The method of claim 1, wherein $R_1$ is a $C_1$-$C_{30}$ hydrocarbyl comprising at least one chiral atom.

3. The method of claim 1, wherein $R_1$ is an N-protected amino acid substituent.

4. The method of claim 3, wherein the N-protected amino acid substituent has a structure according to formula (1), (2), (3), (4), (5), or (6):

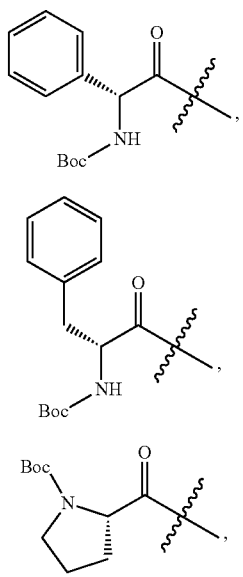

(1)

(2)

(3)

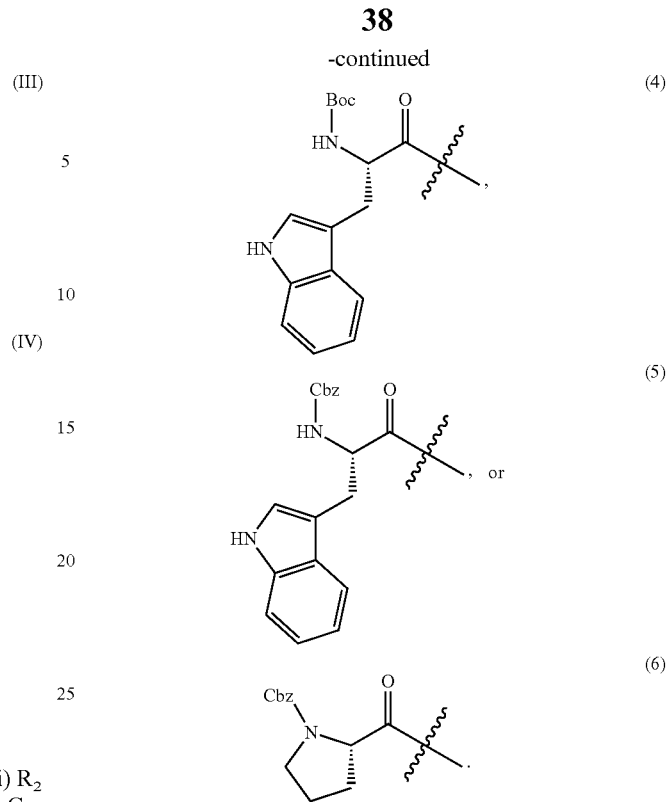

(4)

(5)

(6)

5. The method of claim 1, wherein $R_1$ is a substituent selected from formula (A) or (B);

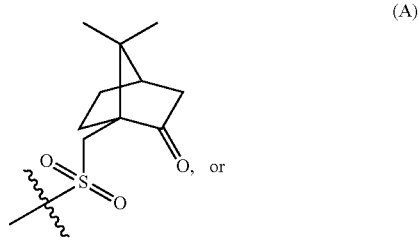

(A)

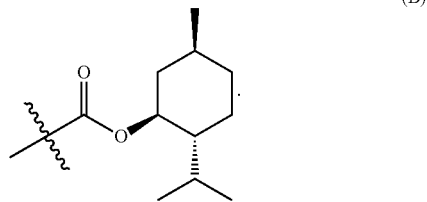

(B)

6. The method of claim 1, wherein $R_2$ is independently selected from the following substituents:

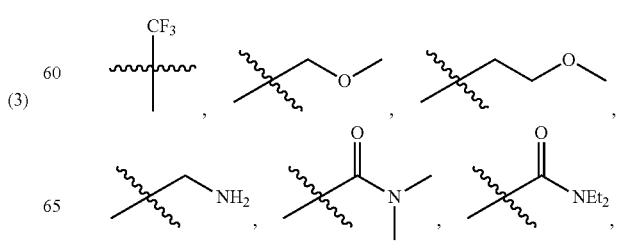

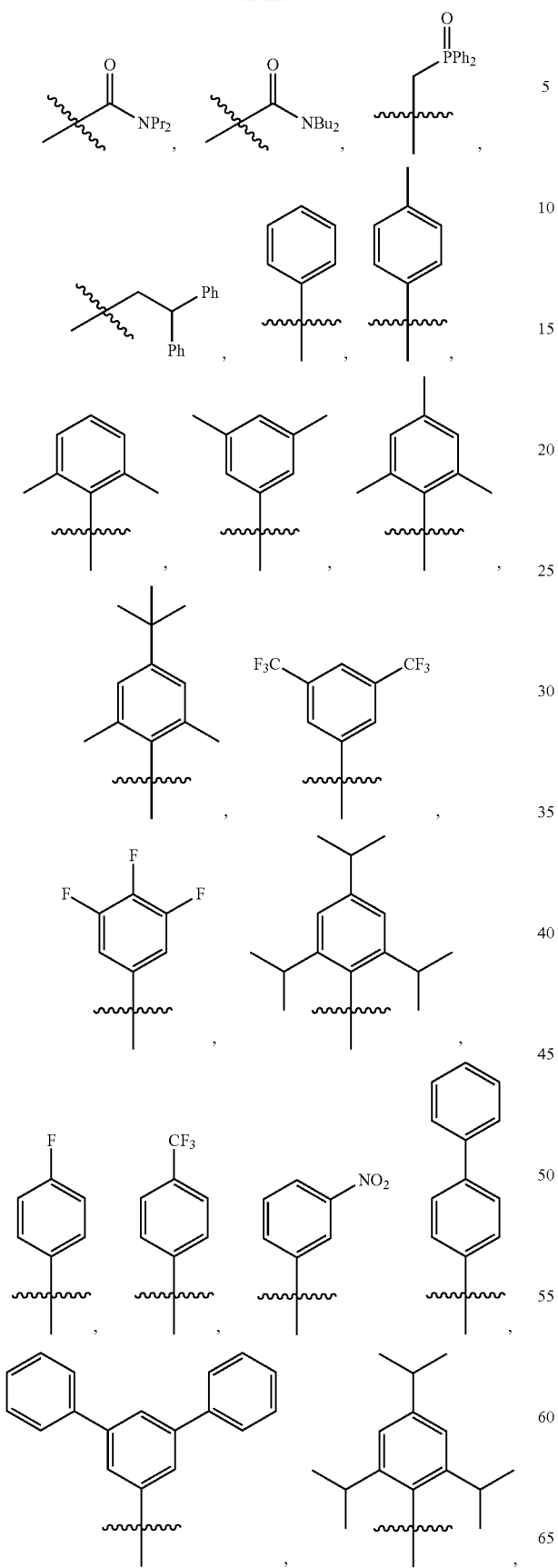
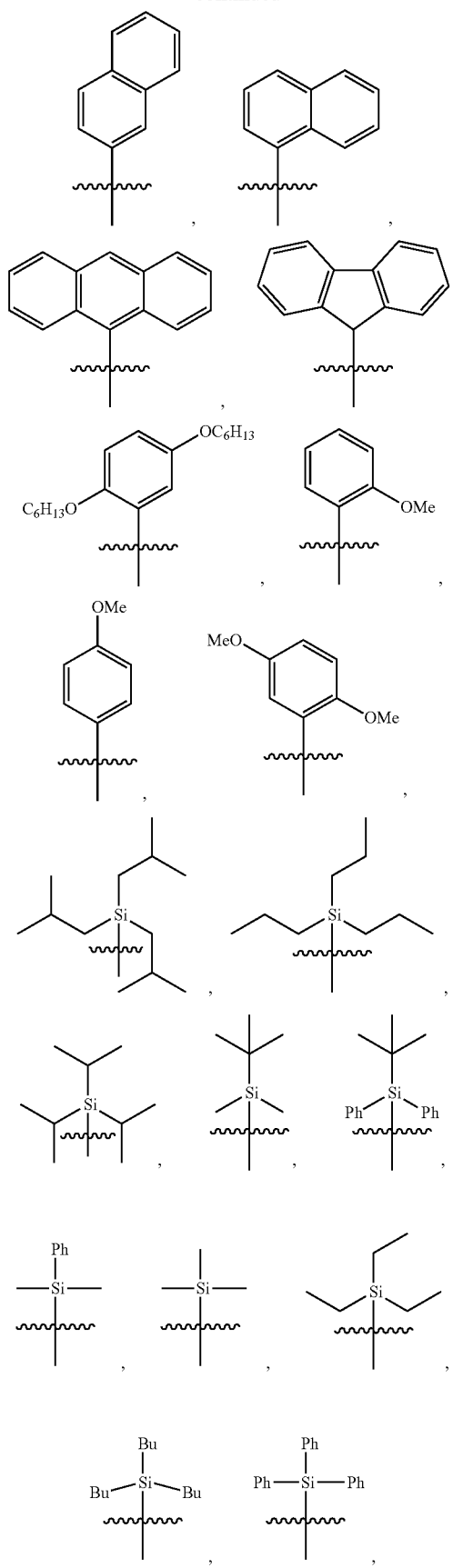

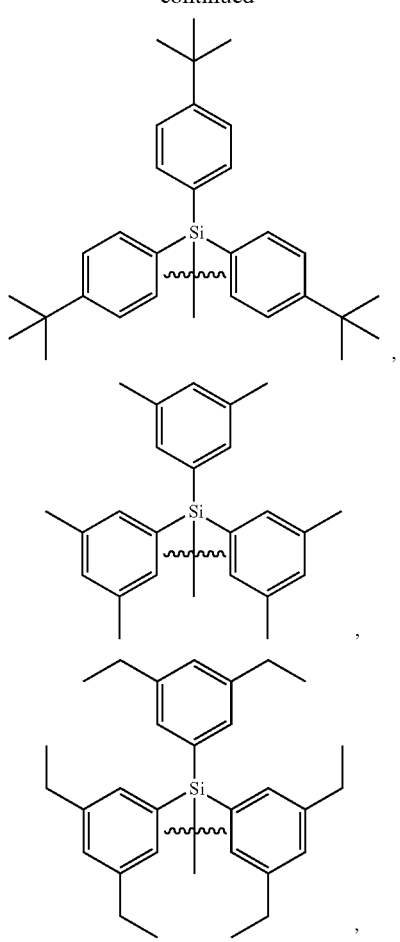
4-β-naphthylphenyl, 4-t-BuC$_6$H$_4$, or 3,5-t-Bu$_2$C$_6$H$_3$.
7. The method of claim 1, wherein R$_3$ is independently selected from the following substituents:
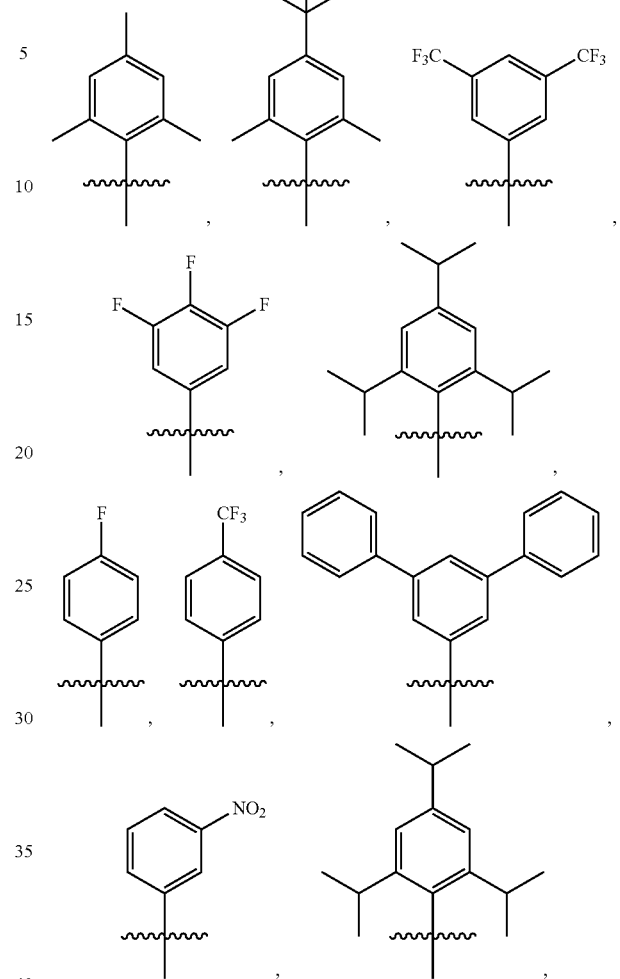
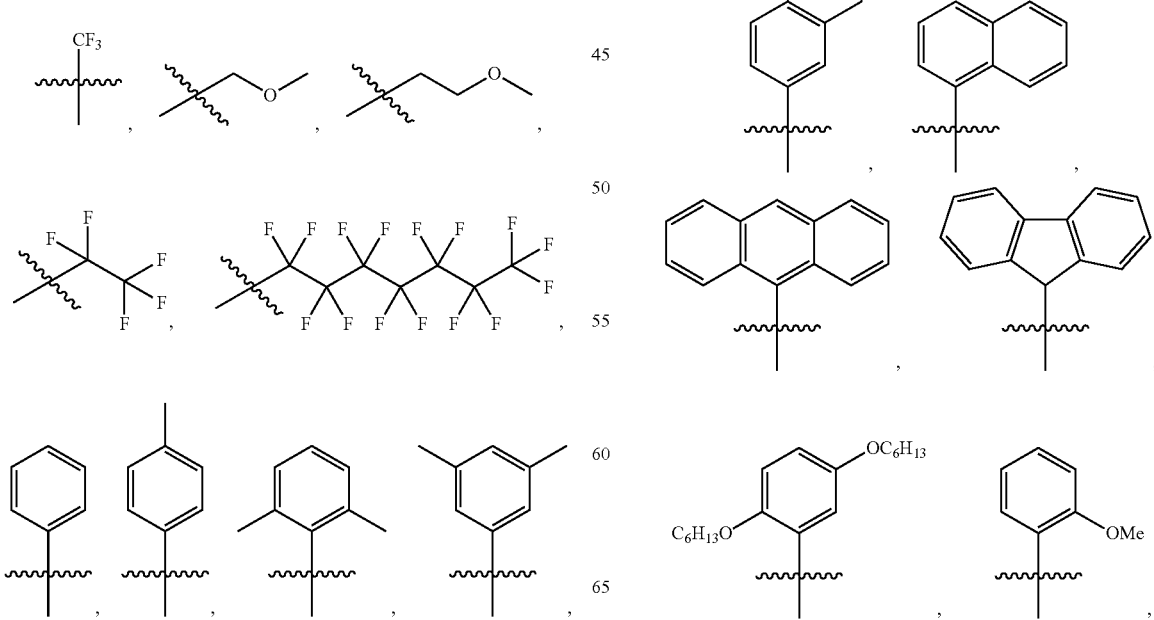

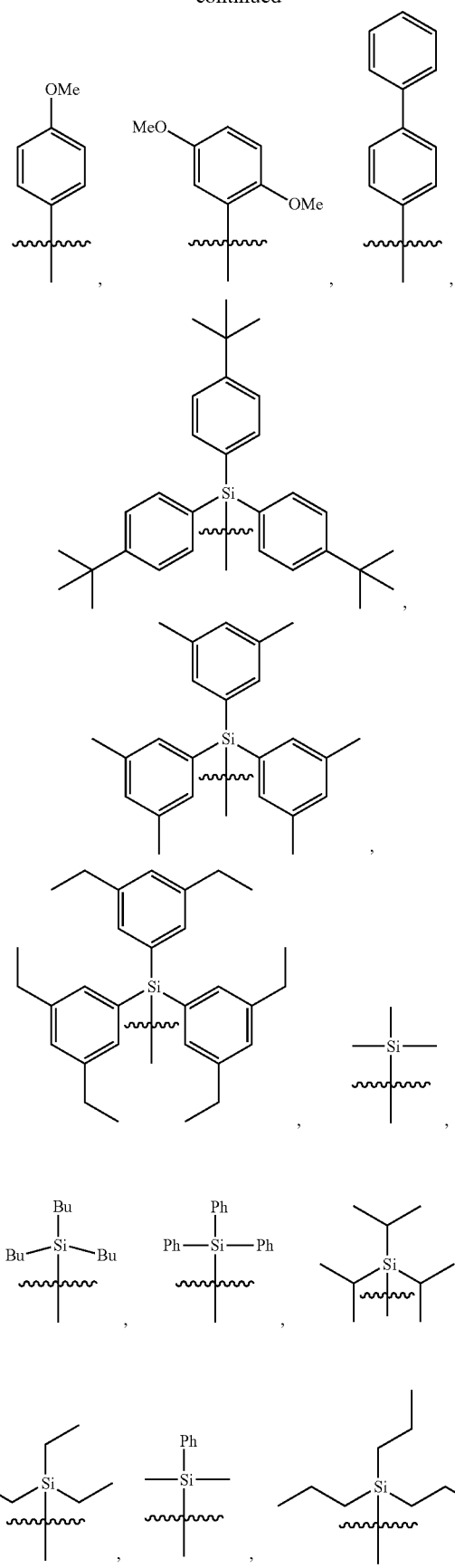

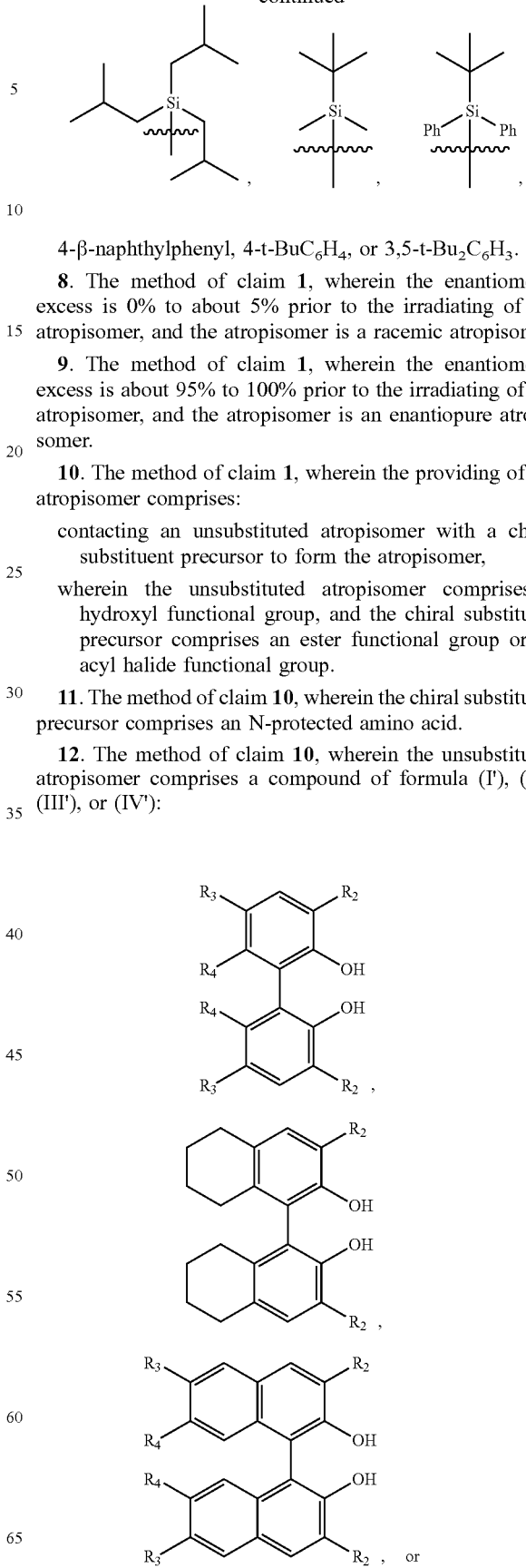

4-β-naphthylphenyl, 4-t-BuC$_6$H$_4$, or 3,5-t-Bu$_2$C$_6$H$_3$.

8. The method of claim 1, wherein the enantiomeric excess is 0% to about 5% prior to the irradiating of the atropisomer, and the atropisomer is a racemic atropisomer.

9. The method of claim 1, wherein the enantiomeric excess is about 95% to 100% prior to the irradiating of the atropisomer, and the atropisomer is an enantiopure atropisomer.

10. The method of claim 1, wherein the providing of the atropisomer comprises:
contacting an unsubstituted atropisomer with a chiral substituent precursor to form the atropisomer,
wherein the unsubstituted atropisomer comprises a hydroxyl functional group, and the chiral substituent precursor comprises an ester functional group or an acyl halide functional group.

11. The method of claim 10, wherein the chiral substituent precursor comprises an N-protected amino acid.

12. The method of claim 10, wherein the unsubstituted atropisomer comprises a compound of formula (I'), (II'), (III'), or (IV'):

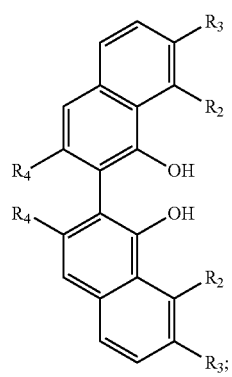
(IV')
wherein (i) R₂ is independently selected from hydrogen, a C₁-C₃₀ hydrocarbyl, or a halogen, (ii) R₃ is independently selected from hydrogen, a C₁-C₃₀ hydrocarbyl, or a halogen, and (iii) R₄ is independently selected from hydrogen or a halogen.
13. The method of claim 12, wherein R₂ is independently selected from the following substituents:
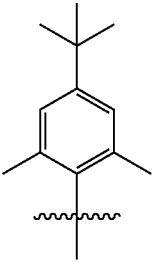
,
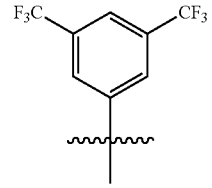
,
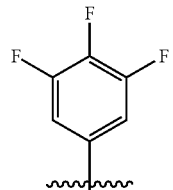
,
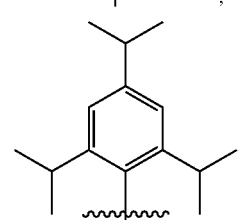
,
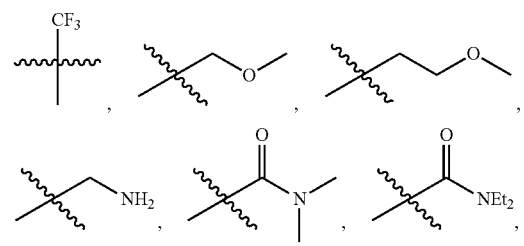
,
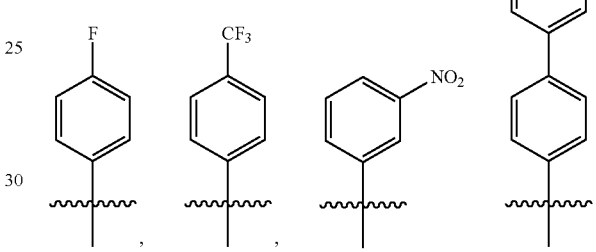
,
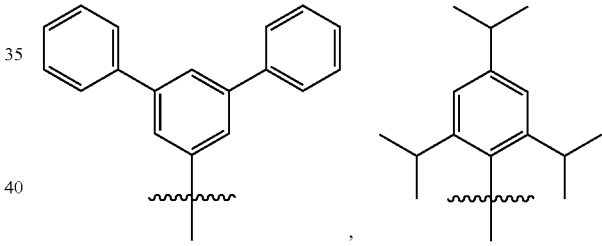
,
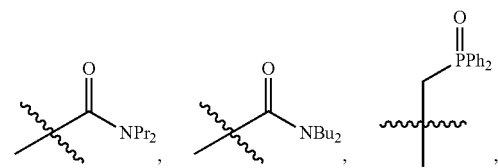
,
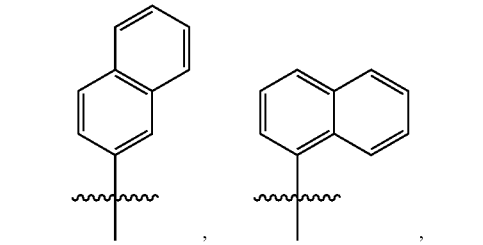
,
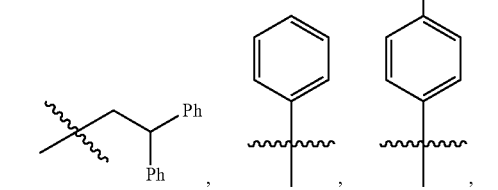
,
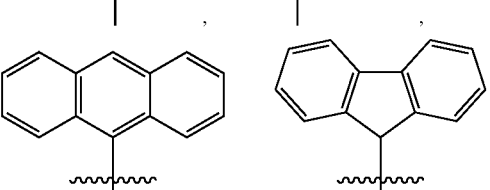
,
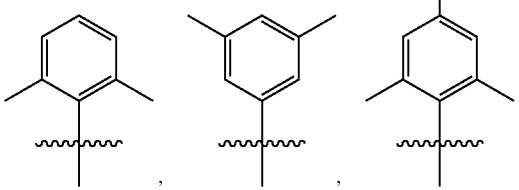
,
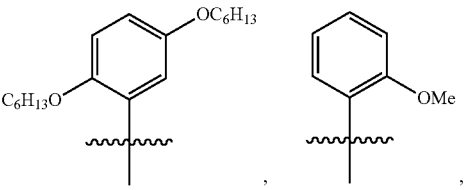
, -continued
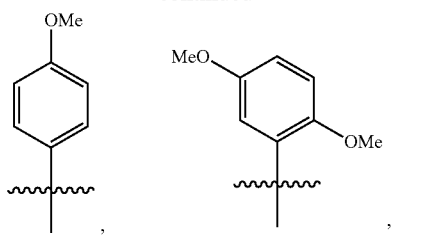
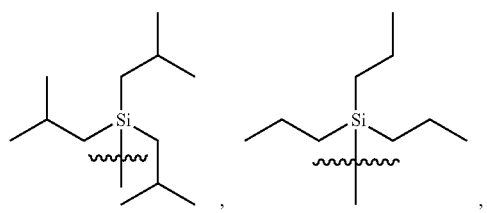
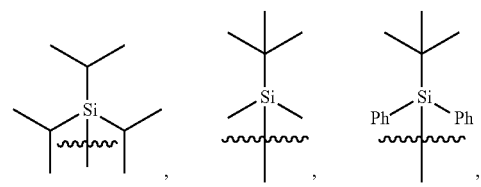
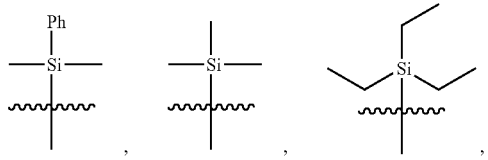
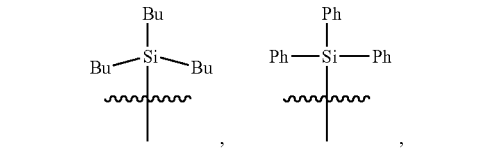
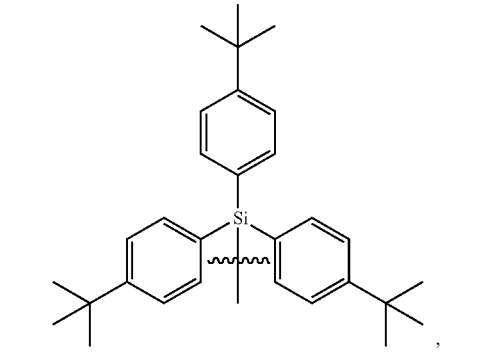
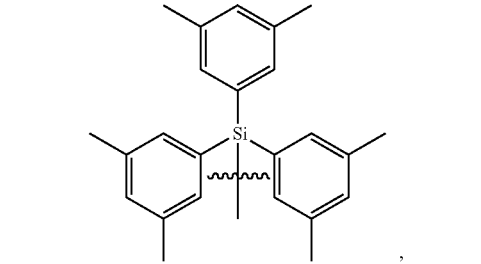
-continued
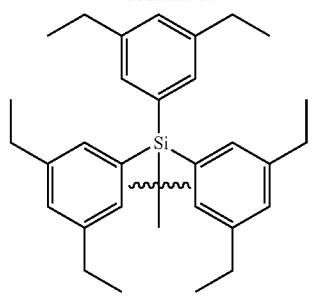
4-β-naphthylphenyl, 4-t-BuC$_6$H$_4$, or 3,5-t-Bu$_2$C$_6$H$_3$.
14. The method of claim 12, wherein R$_3$ is independently selected from the following substituents:
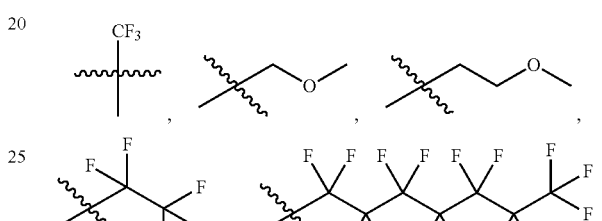
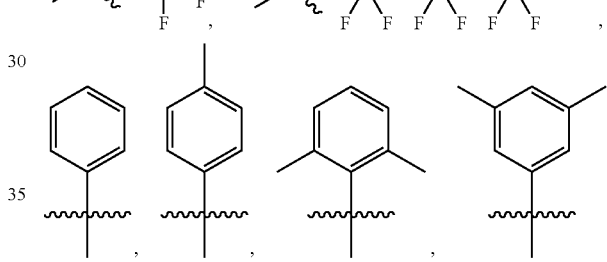
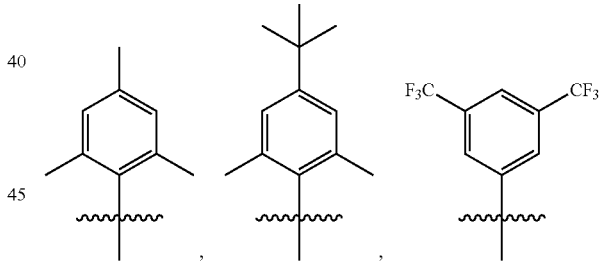
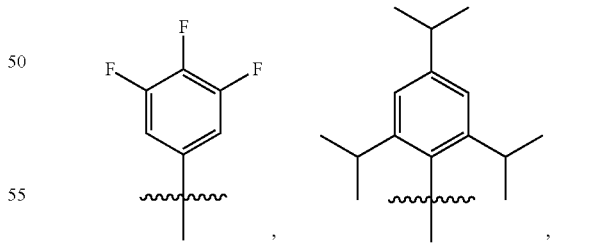
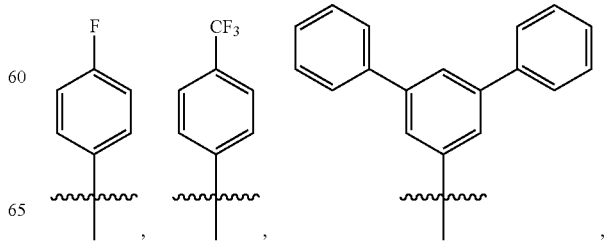

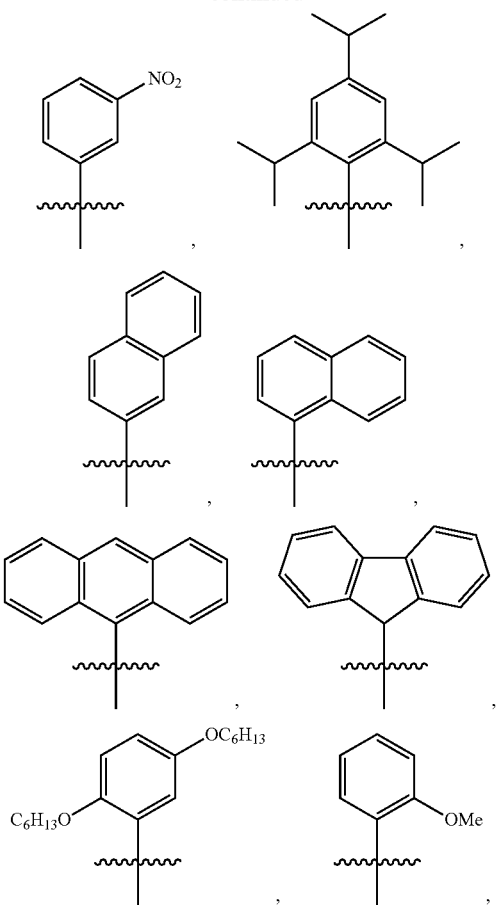

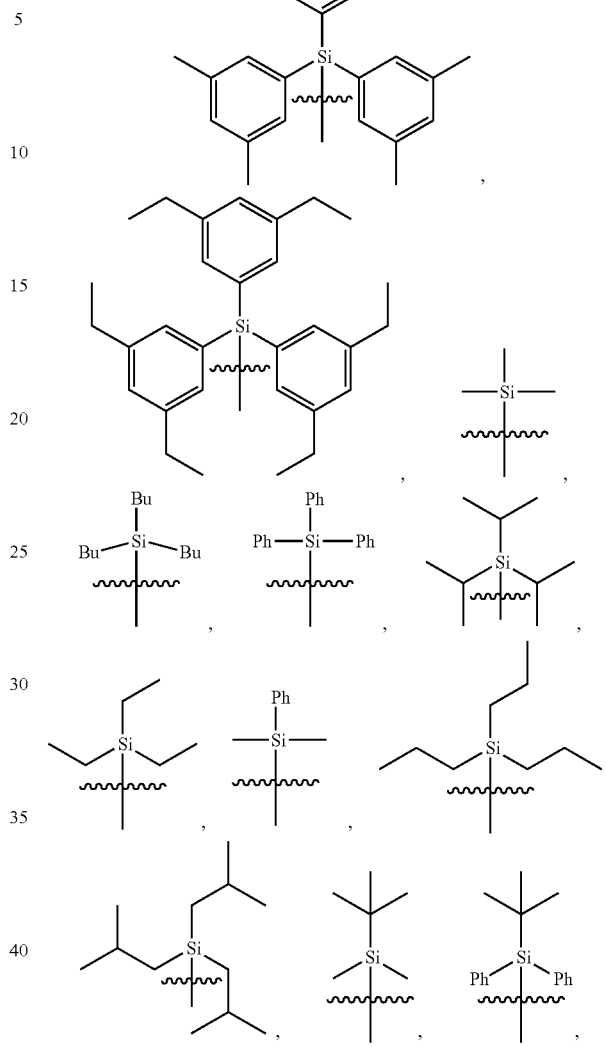

4-β-naphthylphenyl, 4-t-BuC$_6$H$_4$, or 3,5-t-Bu$_2$C$_6$H$_3$.

15. The method of claim 1, wherein the irradiating of the atropisomer comprises exposing the atropisomer to electromagnetic radiation comprising one or more wavelengths of about 10 nm to about 900 nm.

16. The method of claim 1, wherein the atropisomer is contacted with a base during at least a portion of the irradiating of the atropisomer.

17. An atropisomer according to formula (I), (II), (III), or (IV):

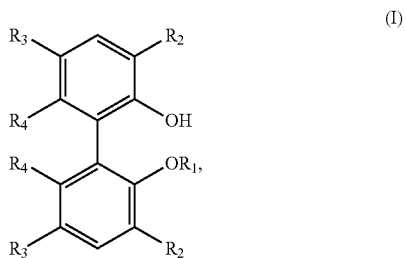

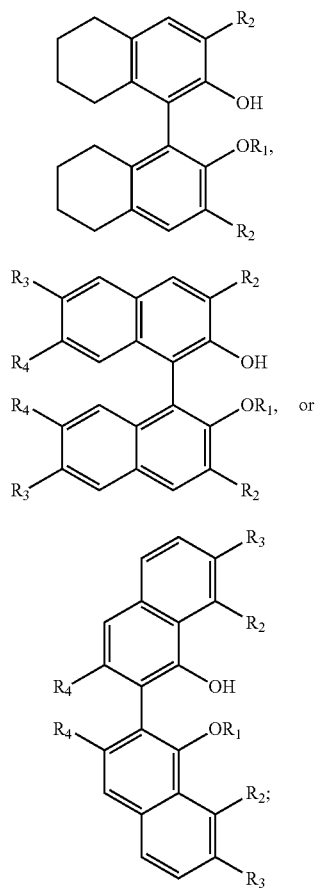

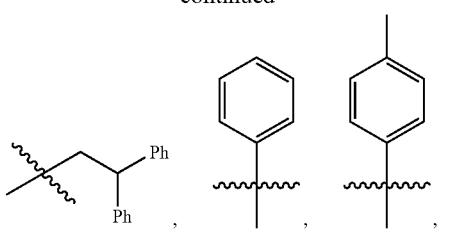
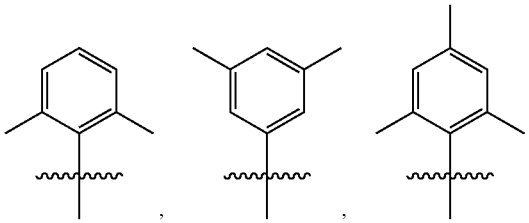
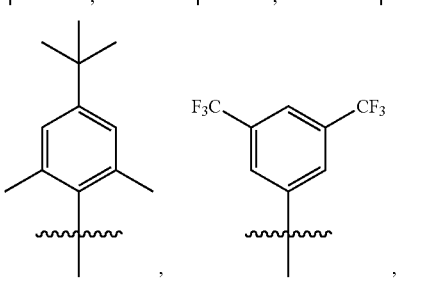
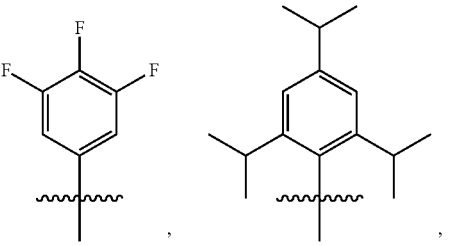

wherein (i) $R_1$ is a $C_1$-$C_{30}$ hydrocarbyl comprising at least one chiral atom, (ii) $R_2$ is independently selected from hydrogen, a $C_1$-$C_{30}$ hydrocarbyl, or a halogen, (iii) $R_3$ is independently selected from hydrogen, a $C_1$-$C_{30}$ hydrocarbyl, or a halogen, and (iv) $R_4$ is independently selected from hydrogen or a halogen; and wherein $R_3$ is independently selected from a $C_1$-$C_{30}$ hydrocarbyl when the atropisomer is of formula (III).

18. The atropisomer of claim 17, wherein $R_1$ is an N-protected amino acid substituent.

19. The atropisomer of claim 17, wherein (i) $R_2$ is independently selected from the following substituents:

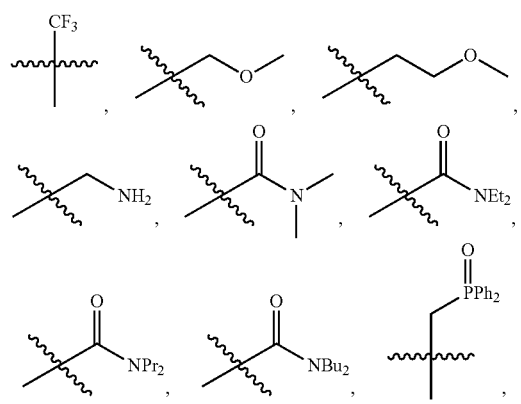

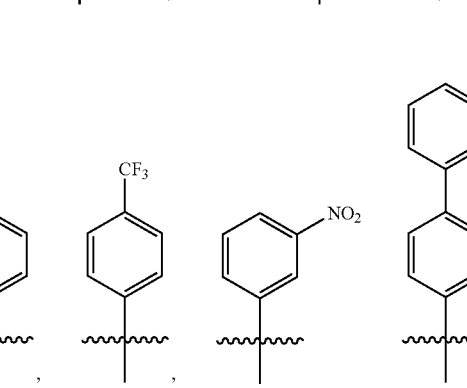

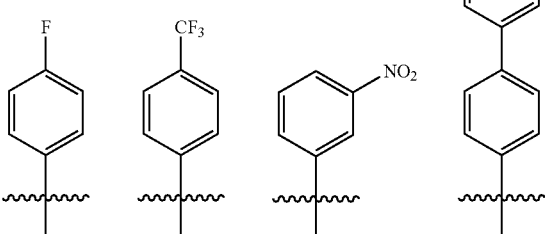

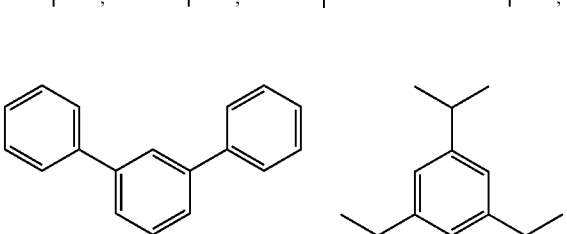

-continued
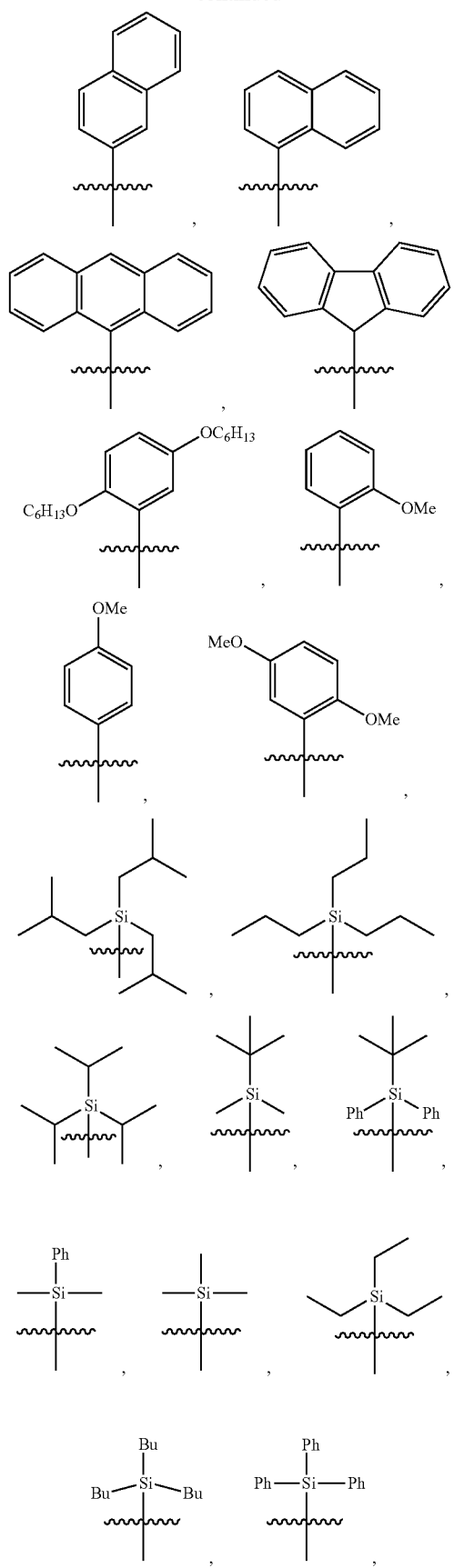
-continued
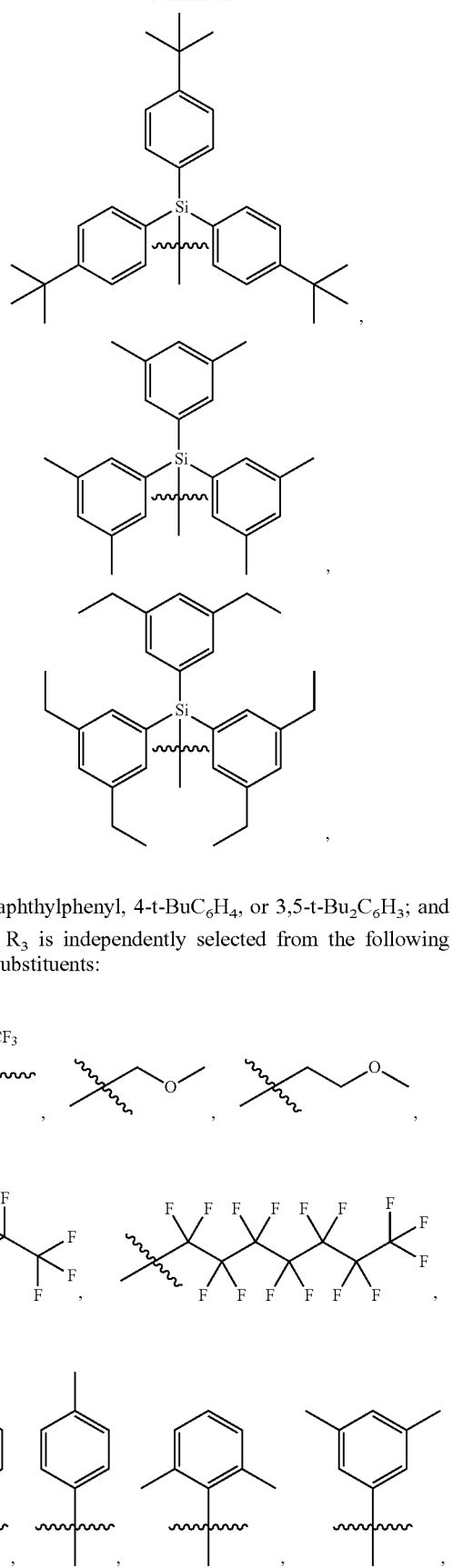
4-β-naphthylphenyl, 4-t-BuC$_6$H$_4$, or 3,5-t-Bu$_2$C$_6$H$_3$; and
(ii) R$_3$ is independently selected from the following substituents:
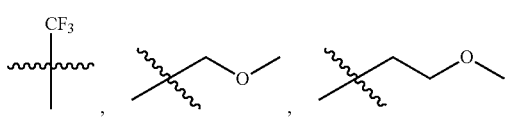
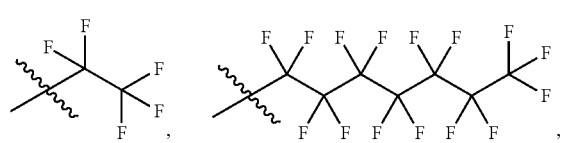
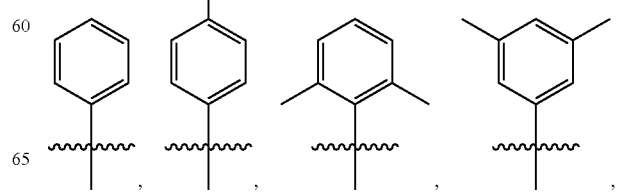

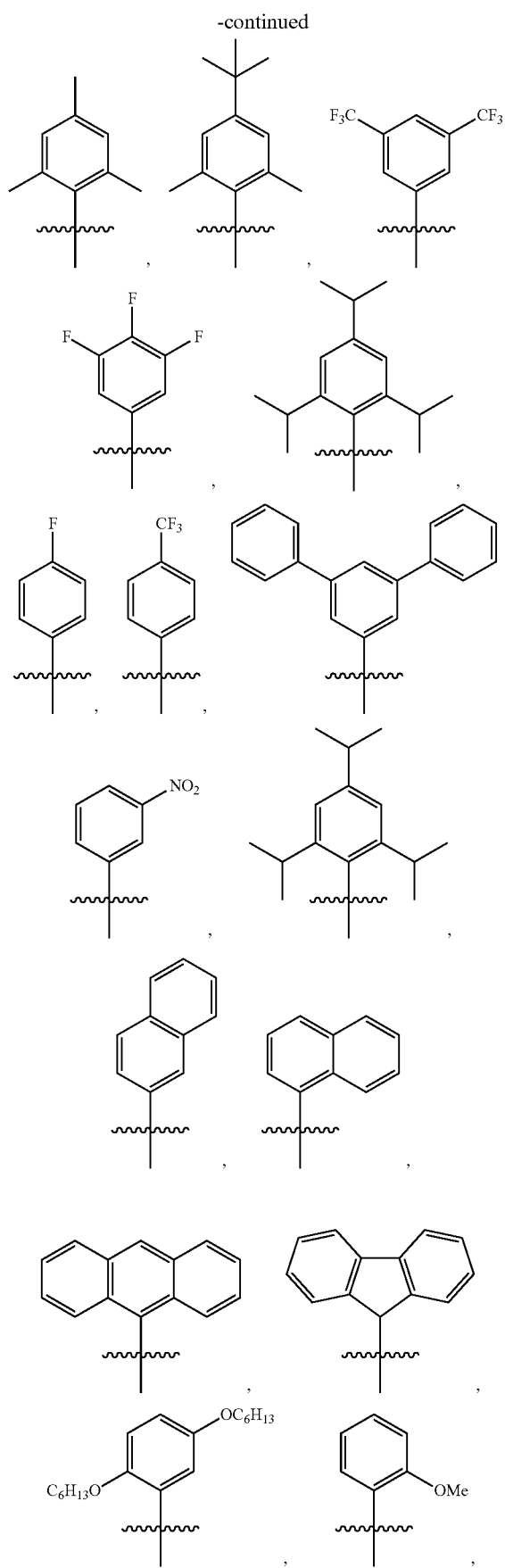
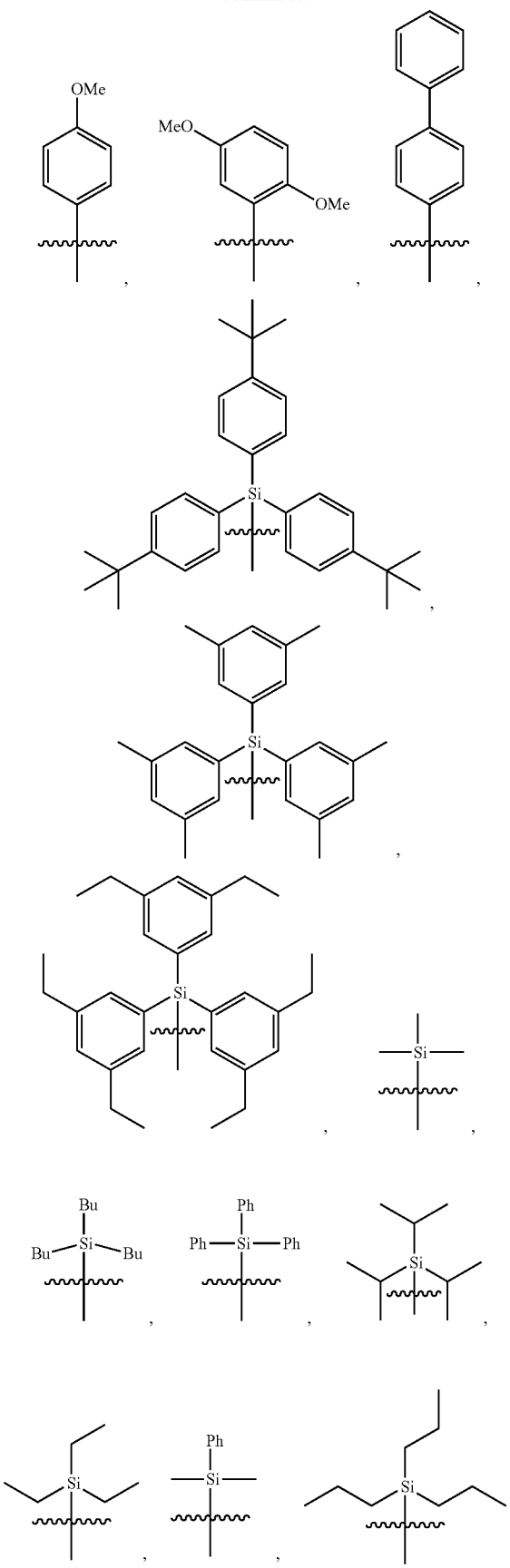

-continued
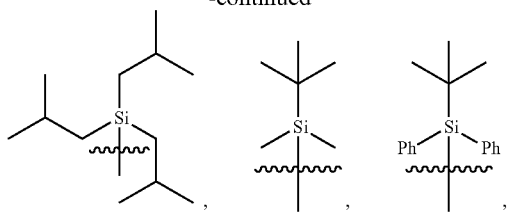
4-β-naphthylphenyl, 4-t-BuC$_6$H$_4$, or 3,5-t-Bu$_2$C$_6$H$_3$.
* * * * *